United States Patent
Purves et al.

(10) Patent No.: US 10,921,246 B2
(45) Date of Patent: Feb. 16, 2021

(54) METHOD OF TUNING A RESONANT CAVITY, AND CAVITY RING-DOWN SPECTROSCOPY SYSTEM

(71) Applicant: Picomole Inc., Moncton (CA)

(72) Inventors: Christopher Quentin Purves, Moncton (CA); Perry F. Kain, Edmonton (CA); Denis Dufour, Montreal (CA)

(73) Assignee: PICOMOLE INC., Moncton (CA)

( * ) Notice: Subject to any disclaimer, the term of this patent is extended or adjusted under 35 U.S.C. 154(b) by 0 days.

(21) Appl. No.: 16/564,662

(22) Filed: Sep. 9, 2019

(65) Prior Publication Data

US 2020/0319099 A1 Oct. 8, 2020

Related U.S. Application Data

(60) Provisional application No. 62/828,750, filed on Apr. 3, 2019.

(51) Int. Cl.
*G01J 3/00* (2006.01)
*G01N 21/39* (2006.01)
(Continued)

(52) U.S. Cl.
CPC .............. *G01N 21/39* (2013.01); *G01J 3/42* (2013.01); *G01N 21/3504* (2013.01);
(Continued)

(58) Field of Classification Search
CPC ............. G01N 21/8507; G01N 21/31; G01N 21/0303; G01N 21/59; G01N 21/05
(Continued)

(56) References Cited

U.S. PATENT DOCUMENTS 3,517,330 A 6/1970 Doyle et al.
4,410,271 A 10/1983 Matthews
(Continued)

FOREIGN PATENT DOCUMENTS

CA 2792032 A1 9/2011
CA 2997070 A1 9/2019
(Continued)

OTHER PUBLICATIONS

Orr et al. "Cavity ringdown spectroscopy with widely tunable swept-frequency lasers," European Quantum Eletronics Conference, 2005 *EQEC '05) Jun. 12-17, 2005, p. 204.
(Continued)

*Primary Examiner* — Md M Rahman
(74) *Attorney, Agent, or Firm* — Millman IP Inc.

(57) ABSTRACT

There is provided a method of tuning a resonant cavity and a cavity ring-down spectroscopy system using the same. A first mirror is actuated at a first end of a resonant cavity to move in a direction between a first position relative to a second mirror at a second end of the resonant cavity, at which a cavity length between the first mirror and the second mirror is less than a resonance length for a laser beam, and a second position relative to the second mirror, at which the cavity length is greater than the resonance length. An event is triggered when the cavity length is proximal to the resonance length. The first mirror is continuously actuated in the direction between the first position and the second position during the event.

26 Claims, 9 Drawing Sheets

(51) Int. Cl.
*G01N 21/3504* (2014.01)
*G01J 3/42* (2006.01)
*G01N 21/552* (2014.01)
*G01N 21/77* (2006.01)

(52) U.S. Cl.
CPC ..... *G01N 21/552* (2013.01); *G01N 2021/391* (2013.01); *G01N 2021/7789* (2013.01)

(58) Field of Classification Search
USPC .......................................................... 356/300
See application file for complete search history.

(56) References Cited

U.S. PATENT DOCUMENTS

| | | |
|---|---|---|
| 4,468,773 A | 8/1984 | Seaton |
| 4,648,714 A | 3/1987 | Benner et al. |
| 4,672,618 A | 6/1987 | Wijntjes et al. |
| 4,779,279 A | 10/1988 | Brown |
| 4,784,486 A | 11/1988 | Van Wagenen et al. |
| 4,964,132 A | 10/1990 | Fischer |
| 5,014,278 A | 5/1991 | Deki |
| 5,029,174 A | 7/1991 | Anderson et al. |
| 5,091,912 A | 2/1992 | Bretenaker et al. |
| 5,135,304 A | 8/1992 | Miles et al. |
| 5,465,728 A | 11/1995 | Phillips |
| 5,528,040 A | 6/1996 | Lehmann |
| 5,573,005 A | 11/1996 | Ueda et al. |
| 5,646,952 A | 7/1997 | Whittley |
| 5,815,277 A | 9/1998 | Zare et al. |
| 5,903,358 A | 5/1999 | Zare et al. |
| 5,912,740 A | 6/1999 | Zare et al. |
| 6,076,392 A | 6/2000 | Drzewiecki |
| 6,084,682 A | 7/2000 | Zare et al. |
| 6,233,052 B1 | 5/2001 | Zare et al. |
| 6,324,191 B1 | 11/2001 | Horvath |
| 6,363,772 B1 | 4/2002 | Berry |
| 6,466,322 B1 | 10/2002 | Paldus et al. |
| 6,479,019 B1 | 11/2002 | Goldstein et al. |
| 6,504,145 B1 | 1/2003 | Romanini et al. |
| 6,540,691 B1 | 4/2003 | Phillips |
| 6,563,583 B2 | 5/2003 | Ortyn et al. |
| 6,582,376 B2 | 6/2003 | Baghdassarian |
| 6,726,637 B2 | 4/2004 | Phillips |
| 6,727,492 B1 | 4/2004 | Ye et al. |
| 6,865,198 B2 | 3/2005 | Taubman |
| 6,952,945 B2 | 10/2005 | O'Brien |
| 7,004,909 B1 | 2/2006 | Patel et al. |
| 7,012,696 B2 | 3/2006 | Orr et al. |
| 7,101,340 B1 | 9/2006 | Braun |
| 7,106,763 B2 | 9/2006 | Tan et al. |
| 7,235,054 B2 | 6/2007 | Eckerbom |
| 7,352,463 B2 | 4/2008 | Bounaix |
| 7,391,517 B2 | 6/2008 | Trebbia et al. |
| 7,450,240 B2 | 11/2008 | Morville et al. |
| 7,541,586 B2 | 6/2009 | Miller |
| 7,555,024 B2 | 6/2009 | Ishaaya et al. |
| 7,569,823 B2 | 8/2009 | Miller |
| 7,606,274 B2 | 10/2009 | Mirov et al. |
| 7,612,885 B2 | 11/2009 | Cole et al. |
| 7,613,216 B2 | 11/2009 | Nakagawa |
| 7,616,123 B2 | 11/2009 | Ridder et al. |
| 7,646,485 B2 | 1/2010 | Tan |
| 7,679,750 B2 | 3/2010 | Li et al. |
| 7,902,534 B2 | 3/2011 | Cole et al. |
| 8,018,981 B2 | 9/2011 | Eckles et al. |
| 8,288,727 B2 | 10/2012 | Cormier et al. |
| 8,659,758 B2 | 2/2014 | Koulikov et al. |
| 8,659,759 B2 | 2/2014 | Koulikov et al. |
| 8,665,442 B2 | 3/2014 | Koulikov et al. |
| 8,885,167 B2 | 11/2014 | Koulikov et al. |
| 8,982,352 B1 | 3/2015 | Hoffnagle et al. |
| 9,014,221 B2 | 4/2015 | Kub et al. |
| 9,097,583 B2 | 8/2015 | Gupta et al. |
| 9,194,742 B2 | 11/2015 | Kachanov et al. |
| 9,212,990 B1 | 12/2015 | Muraviev |
| 9,568,465 B2 | 2/2017 | Rihani et al. |
| 9,625,702 B2 | 4/2017 | Hodges et al. |
| 9,671,332 B2 | 6/2017 | Christensen |
| 9,778,110 B1 | 10/2017 | Rella et al. |
| 9,918,661 B2 | 3/2018 | Cormier et al. |
| 10,034,621 B2 | 7/2018 | Wondka et al. |
| 10,130,284 B2 | 11/2018 | Johnson |
| 10,139,392 B2 | 11/2018 | Kaariainen et al. |
| 10,168,275 B2 | 1/2019 | Orcutt |
| 10,194,833 B2 | 2/2019 | Cormier |
| 10,234,381 B2 | 3/2019 | Koulikov |
| 10,330,592 B2 | 6/2019 | Koulikov |
| 10,401,281 B2 | 9/2019 | Koulikov |
| 10,499,819 B2 | 12/2019 | Wondka et al. |
| 10,527,492 B2 | 1/2020 | Bouzid |
| 2003/0109794 A1 | 6/2003 | Phillips |
| 2004/0022281 A1 | 2/2004 | Steffens et al. |
| 2004/0137637 A1 | 7/2004 | Wang et al. |
| 2004/0142484 A1 | 7/2004 | Berlin et al. |
| 2004/0162500 A1 | 8/2004 | Kline |
| 2004/0190563 A1 | 9/2004 | Gendron |
| 2005/0134836 A1 | 6/2005 | Paldus et al. |
| 2005/0177056 A1 | 8/2005 | Giron et al. |
| 2005/0177057 A1 | 8/2005 | Friedman et al. |
| 2005/0201428 A1 | 9/2005 | Cotteverte et al. |
| 2006/0200037 A1 | 9/2006 | Falasco |
| 2007/0062255 A1 | 3/2007 | Talton |
| 2007/0091941 A1 | 4/2007 | Mori et al. |
| 2007/0133001 A1 | 6/2007 | Cox et al. |
| 2007/0268941 A1* | 11/2007 | Kim ........................ H01S 5/141 372/22 |
| 2008/0091085 A1 | 4/2008 | Urushihata et al. |
| 2008/0139021 A1 | 6/2008 | Suzuki et al. |
| 2008/0170597 A1 | 7/2008 | van der Veer |
| 2009/0201957 A1 | 8/2009 | Brotherton-Ratcliffe |
| 2009/0306527 A1 | 12/2009 | Kubo et al. |
| 2010/0002234 A1 | 1/2010 | Cormier et al. |
| 2010/0074089 A1 | 3/2010 | Smith et al. |
| 2011/0072887 A1 | 3/2011 | Oki |
| 2011/0216311 A1 | 9/2011 | Kachanov et al. |
| 2011/0269632 A1 | 11/2011 | Haick |
| 2011/0295140 A1 | 12/2011 | Zaidi et al. |
| 2012/0143805 A1 | 6/2012 | Gold et al. |
| 2012/0250706 A1 | 10/2012 | Stiens et al. |
| 2012/0266883 A1 | 10/2012 | Taylor et al. |
| 2012/0309048 A1 | 12/2012 | Ratcliffe et al. |
| 2013/0144561 A1 | 6/2013 | Harb et al. |
| 2013/0303929 A1 | 11/2013 | Martino et al. |
| 2014/0293283 A1 | 10/2014 | Farooq et al. |
| 2014/0320856 A1 | 10/2014 | McKeever et al. |
| 2015/0032019 A1 | 1/2015 | Acker et al. |
| 2015/0077747 A1* | 3/2015 | Smith ..................... G01N 21/31 356/318 |
| 2015/0335267 A1 | 11/2015 | Cormier et al. |
| 2016/0069795 A1* | 3/2016 | Koulikov ............... G02B 7/181 356/437 |
| 2016/0174875 A1 | 6/2016 | Forster et al. |
| 2016/0285236 A1 | 9/2016 | Yvind |
| 2017/0074857 A1 | 3/2017 | Dennis et al. |
| 2018/0059003 A1 | 3/2018 | Jourdainne |
| 2018/0156718 A1 | 6/2018 | Fleisher et al. |
| 2018/0202918 A1 | 7/2018 | Tanaka et al. |
| 2018/0202923 A1 | 7/2018 | Kageyama et al. |
| 2018/0214050 A1 | 8/2018 | Purves |
| 2018/0261974 A1 | 9/2018 | Purves et al. |
| 2018/0350304 A1* | 12/2018 | Ishii ...................... G09G 3/2022 |
| 2019/0265159 A1 | 8/2019 | Koulikov |
| 2019/0265160 A1 | 8/2019 | Koulikov |
| 2019/0271641 A1 | 9/2019 | Koulikov |
| 2019/0301933 A1 | 10/2019 | Allison |
| 2019/0323955 A1 | 10/2019 | Koulikov |

FOREIGN PATENT DOCUMENTS

| | | |
|---|---|---|
| CN | 101470072 A | 7/2009 |
| CN | 102316801 B | 1/2012 |
| CN | 102798631 A | 11/2012 |
| CN | 102841082 A | 12/2012 |

(56) References Cited

FOREIGN PATENT DOCUMENTS

| CN | 102264292 | B  | 5/2014  |
|----|-----------|----|---------|
| CN | 106908389 | A  | 6/2017  |
| CN | 107037003 | A  | 8/2017  |
| CN | 109856054 | A  | 6/2019  |
| DE | 2130331   | A1 | 3/1977  |
| DE | 2723939   | A1 | 12/1978 |
| DE | 3819687   | A1 | 12/1989 |
| DE | 10156149  | A1 | 6/2003  |
| EP | 557658    | A1 | 9/1993  |
| EP | 600711    | A2 | 6/1994  |
| EP | 1535047   | B1 | 6/2005  |
| EP | 1304955   | B1 | 12/2008 |
| EP | 1997198   | B1 | 6/2012  |
| EP | 1418842   | B1 | 7/2012  |
| EP | 3037805   | A1 | 6/2016  |
| EP | 2745097   | B1 | 2/2018  |
| EP | 3419122   | A1 | 12/2018 |
| EP | 3467473   | A1 | 4/2019  |
| GB | 1019295   | A  | 2/1966  |
| JP | 2001194299 | A | 7/2001  |
| JP | 2006189392 | A | 7/2006  |
| JP | 2006226727 | A | 8/2006  |
| JP | 2010243270 | A | 10/2010 |
| JP | 2013011620 | A | 1/2013  |
| JP | 5341519   | B2 | 11/2013 |
| JP | 5537174   | B2 | 7/2014  |
| JP | 2016503904 | A | 2/2016  |
| WO | 2090935   |    | 11/2002 |
| WO | 2005038436 | A2 | 4/2005 |
| WO | 2005076875 | A2 | 8/2005 |
| WO | 2005088274 | A1 | 9/2005 |
| WO | 2017142644 | A1 | 12/2007 |
| WO | 2011117572 | A1 | 9/2011 |
| WO | 2012004794 | A1 | 1/2012 |
| WO | 2014070952 | A1 | 5/2014 |
| WO | 2018142027 | A1 | 8/2018 |
| WO | 2019239827 | A1 | 12/2019 |

OTHER PUBLICATIONS

ISR for PCT/CA2007/002306 dated Apr. 17, 2008.
Office action for CA2671122 dated Jun. 13, 2011.
Harren et al., Photoacoustic Spectroscopy in Trace Gas Monitoring, encyclopedia of Analytical Chemistry, pp. 2203-2226, J. Wiley and Sons, 2000.
Freed, C., Status of CO2 Isotope Lasers and Their Applications in Tunable Laser Spectroscopy, IEEE Journal of Quantum Electronics, vol. QE-18, No. 8, 1982.
Sharpe et al., "Gas Phase Databases for Quantitative Infrared Spectroscopy," Applied Spectroscopy, vol. 58, No. 12, 2004.
Akaike, H., "A new look at the statistical model identification," IEEE Transactions on Automatic Control, 19(6): 716-723, 1974.
Cormier, John G., "Development of an Infrared Cavity Ringdown Spectroscopy Experiment and Measurements of Water Vapor Continuum Absorption.," Thesis, 2002.
Kurochkin et al., "Three Mirror Cavity CO2 Lser for Inactivity Saturated-Absorption Spectroscopy." Optical Spectroscopy, vol. 65, No. 2, pp. 265-267, Aug. 1988.
Office Action for U.S. Appl. No. 12/517,036 dated Dec. 14, 2011.
Fuchs, D., et al., "Decline of exhaled isoprene in lung cancer patients correlates with immune activation," Journal of breath research 6.2 (2012): 027101+B8.
Ligor, Magdalena, et al., "Determination of volatile organic compounds of exhaled breath of patients with lung cancer using solid phase microextraction and gas chromatography mass spectrometry," Clinical chemistry and laboratory medicine 47.5 (2009): 550-560.
Vaughan, Christina, et al., "Automated determination of seven phenolic compounds in mainstream tobacco smoke," Nicotine and Tobacco Research 10.7 (2008): 1261-1268.
Cope, et al., "Effects of ventilation on the collection of exhaled breath in humans," J. App l Physiol 96: 1371-1379: 2004.
Office action for U.S. Appl. No. 14/720,447 dated Apr. 6, 2017.
Office action for U.S. Appl. No. 14/720,447 dated Apr. 19, 2018.
Final office action for U.S. Appl. No. 14/720,447 dated Sep. 13, 2017.
English translation of DE102013215640A1.
Office action for U.S. Appl. No. 14/720,456 dated Jun. 14, 2017.
Office action for U.S. Appl. No. 15/920,212 dated Jun. 27, 2019.
Final Office action for U.S. Appl. No. 15/920,212 dated Oct. 3, 2019.
Notice of Allowance for U.S. Appl. No. 15/920,212 dated Jan. 23, 2020.
International Search Report and Written Opinion for PCT/CA2020/050252 dated May 12, 2020.
International Search Report and Written Opinion for PCT/CA2020/050250 dated May 22, 2020.
International Search Report and Written Opinion for PCT/CA2020/050/249 dated Apr. 29, 2020.
International Search Report and Written Opinion for PCT/CA2020/050248 dated Jun. 11, 2020.
Office action for U.S. Appl. No. 15/917,225 dated Mar. 9, 2020.
Office action for U.S. Appl. No. 15/917,225 dated May 14, 2020.

\* cited by examiner

METHOD OF TUNING A RESONANT CAVITY, AND CAVITY RING-DOWN SPECTROSCOPY SYSTEM

CROSS-REFERENCE TO RELATED APPLICATIONS

This application claims the benefit of U.S. Provisional Application No. 62/828,750, filed Apr. 3, 2019, the contents of which are incorporated herein by reference in their entirety.

FIELD

The specification relates generally to resonant cavities, and, in particular, to a method for tuning a resonant cavity, and a cavity ring-down spectroscopy system.

BACKGROUND OF THE DISCLOSURE

Cavity ring-down spectroscopy ("CRDS") is an approach that is generally used to analyze a gaseous sample via their absorption spectra. A typical CRDS system employs a laser generating a beam that is directed into a cavity of a chamber having two highly reflective mirrors. The beam is normally within the visible light spectrum, or the near infrared ("IR") spectrum, and is tuned to a single wavelength. The beam is then reflected repeatedly between the mirrors, which allow a fraction of the light to escape the ring-down cavity.

In order to "fill" the ring-down cavity, the length of the cavity has to be in tune with the laser wavelength. This is generally done by adjusting the position of one of the two mirrors. When the laser is in resonance with a cavity mode, intensity builds up in the cavity due to constructive interference. When the light entering the cavity is extinguished, the intensity of the light in the ring-down cavity, when empty, decays at a pre-determined rate. A small fraction of the light is not reflected by the mirrors and escapes the ring-down cavity. The intensity of the escaping light is measured by a sensor component to determine the decay rate.

When the gaseous sample is placed in the ring-down cavity, analytes present in the gaseous sample absorb some of the light, thereby accelerating the decay of the intensity of the light in the ring-down cavity. Absorption spectra are generated by measuring the decay times of the light in the presence of the gaseous sample at specific wavelengths relative to the decay times of the light in the absence of the gaseous sample at these wavelengths. Identification and quantification of individual analytes in the gaseous sample can be achieved via a number of methods, such as, for example, the performance of a linear regression of the measured absorption spectra for the gaseous sample with the known absorption spectra of various analytes.

In order to "fill" the ring-down cavity through constructive interference, the length of the ring-down cavity has to be in tune with the laser wavelength. This is achieved by adjusting the cavity length by moving one of the mirrors relative to the other of the mirrors. The mirror is typically moved by one or more piezoelectric (referred to herein as "piezo") actuators driven by a piezo driver to adjust the length of the ring-down cavity. Piezo drivers, however, produce discrete output voltages, resulting in discrete positions in which the mirror can be positioned, thus providing discrete cavity lengths between the mirrors. If none of the discrete positions and, thus, the discrete cavity lengths lead to constructive interference of the laser light of the particular wavelength, the ring-down cavity may be difficult to fill in order to perform a ring-down event. More complex/expensive piezo drivers can have more fine resolutions, but their cost can be prohibitive.

SUMMARY OF THE DISCLOSURE

In one aspect, there is provided a method of tuning a resonant cavity, comprising actuating a first mirror at a first end of a resonant cavity to move in a direction between a first position relative to a second mirror at a second end of the resonant cavity, at which a cavity length between the first mirror and the second mirror is less than a resonance length for a laser beam, and a second position relative to the second mirror, at which the cavity length is greater than the resonance length, triggering an event when the cavity length is proximal to the resonance length, and continuing to actuate the first mirror in the direction between the first position and the second position during the event.

The event can be a first event, the direction can be a first direction, and the method can further include, after the continuing, actuating the first mirror to move in a second direction opposite the first direction and towards the first position, triggering a second event when the cavity length is proximal to the resonance length, and continuing to actuate the first mirror in the second direction between the second position and the first position during the second event.

The method can further include repeatedly actuating the first mirror to move in the first direction and the second direction, triggering events when the cavity length is proximal to the resonance length, and continuing to actuate the first mirror during the events.

The method can further include applying a voltage waveform to at least one piezo actuator coupled to the first mirror to actuate the first mirror between the first position and the second position.

The waveform can be sinusoidal.

The method can further include adding a base voltage to the waveform voltage applied to the at least one piezo actuator.

The method can further include controlling the base voltage to locate a light intensity peak via a light detector coupled to the resonant cavity, the peak light intensity occurring at the resonance length.

The method can further include selecting an amplitude for the voltage waveform applied to the at least one piezo actuator that actuates the first mirror less than one wavelength of a laser beam illuminating the resonant cavity, and controlling the base voltage so that two light intensity peaks are detected during each period of the voltage waveform.

The method can further include controlling the base voltage so that adjacent light intensity peaks are spaced by one half of a period of the voltage waveform.

The method can further include triggering the events to occur when a detected light intensity achieves a threshold intensity.

The events can be ring-down events.

The light detector can be coupled to a timing circuit, the timing circuit can be coupled to one of an optical modulator and a laser to extinguish the laser beam from the laser or detune the laser for the resonant cavity.

The method can further include determining expected recurrence times for a threshold intensity, and triggering the extinguishing of the laser beam or the detuning of the laser beam for the resonant cavity at the expected recurrence times for the threshold intensity.

The method can further include detecting an intensity of light in the resonant cavity via a light detector, wherein the triggering comprises triggering when a light intensity in the resonant cavity detected by the light detector achieves a threshold intensity.

The light detector can be coupled to timing circuit, and the timing circuit can be coupled to one of an optical modulator and a laser to extinguish the laser beam from the laser or detune the laser.

In another aspect, there is provided a method of tuning a resonant cavity, comprising altering a cavity length between a first mirror at a first end of a resonant cavity and a second mirror at a second end of the resonant cavity between a first cavity length that is less than a resonance length for a laser beam, and a second cavity length that is greater than the resonance length for the laser beam; triggering an event when the cavity length is proximal to the resonance length; and continuing to alter the cavity length towards the second cavity length during the event.

In a further aspect, there is provided a method of tuning a resonant cavity, comprising: actuating a first mirror at a first end of a resonant cavity to move in a direction between a first position relative to a second mirror at a second end of the resonant cavity, at which a cavity length between the first mirror and the second mirror is less than a resonance length for a laser beam, and a second position relative to the second mirror, at which the cavity length is greater than the resonance length; triggering the extinguishing of a laser beam illuminating the resonant cavity or the detuning of the laser beam for the resonant cavity when the cavity length is proximal to the resonance length; and continuing to actuate the first mirror in the direction between the first position and the second position while a light detector registers light intensity in the resonant cavity.

The direction can be a first direction, and the method can further include, after the continuing, triggering the illumination of the laser beam or the retuning of the laser beam for the resonant cavity, actuating the first mirror to move in a second direction opposite the first direction and towards the first position, triggering the extinguishing of the laser beam or the detuning of the laser beam for the resonant cavity, and continuing to actuate the first mirror in the second direction between the second position and the first position while the light detector registers light intensity in the resonant cavity.

The method can further include applying a sinusoidal waveform to at least one piezo actuator coupled to the first mirror to actuate the first mirror between the first position and the second position.

The method can further include adding a base voltage to the waveform voltage applied to the at least one piezo actuator.

The method can further include controlling the base voltage to locate a light intensity peak via a light detector coupled to the resonant cavity, the peak light intensity occurring at the resonance length.

The method can further include selecting an amplitude for the voltage waveform applied to the at least one piezo actuator that actuates the first mirror less than one wavelength of a laser beam illuminating the resonant cavity, and controlling the base voltage so that two light intensity peaks are detected during each period of the voltage waveform.

The method can further include controlling the base voltage so that adjacent light intensity peaks are spaced by one half of a period of the voltage waveform.

The cavity length being proximal to the resonance length can be detected by a detected light intensity achieving a threshold intensity.

The light detector can be coupled to a timing circuit, and the timing circuit can be coupled to one of an optical modulator and a laser to extinguish the laser beam from the laser or detune the laser for the resonant cavity.

The method can further include determining expected recurrence times for achievement of a threshold intensity as a proxy for when the cavity length is proximal to the resonance length.

In yet another aspect, there is provided a cavity ring-down spectroscopy system, comprising: a resonant cavity having a first mirror at a first end of the resonant cavity and a second mirror at a second end of the resonant cavity; a light detector coupled to the resonant cavity to measure a light intensity therein; at least one piezo actuator coupled to the first mirror to actuate the first mirror; and a control module coupled to the at least one piezo actuator to control the at least one piezo actuator to actuate the first mirror to move in a direction between a first position relative to the second mirror, at which a cavity length between the first mirror and the second mirror is less than a resonance length for a laser beam, and a second position relative to the second mirror, at which the cavity length is greater than the resonance length, trigger the extinguishing of a laser beam illuminating the resonant cavity or the detuning of the laser beam for the resonant cavity when the cavity length is proximal to the resonance length, and continue to actuate the first mirror in the direction between the first position and the second position while the light detector registers the light intensity in the resonant cavity.

The direction can be a first direction, and the control module can trigger the illumination of the laser beam or the retuning of the laser beam for the resonant cavity, actuate the first mirror to move in a second direction opposite the first direction and towards the first position, trigger the extinguishing of the laser beam or the detuning of the laser beam for the resonant cavity, and continue to actuate the first mirror in the second direction between the second position and the first position while the light detector registers light intensity in the resonant cavity.

The control module can apply a sinusoidal waveform to at least one piezo actuator coupled to the first mirror to actuate the first mirror between the first position and the second position.

The control module can add a base voltage to the waveform voltage applied to the at least one piezo actuator.

The control module can control the base voltage to locate a light intensity peak via a light detector coupled to the resonant cavity, the peak light intensity occurring at the resonance length.

The control module can select an amplitude for the voltage waveform applied to the at least one piezo actuator that actuates the first mirror less than one wavelength of a laser beam illuminating the resonant cavity, and control the base voltage so that two light intensity peaks are detected during each period of the voltage waveform.

The control module can control the base voltage so that adjacent light intensity peaks are spaced by one half of a period of the voltage waveform.

The control module can determine that the cavity length is proximal to the resonance length when a detected light intensity achieves a threshold intensity.

The light detector can be coupled to a timing circuit, and the timing circuit can be coupled to one of an optical modulator and a laser to extinguish the laser beam from the laser or detune the laser for the resonant cavity.

Other technical advantages may become readily apparent to one of ordinary skill in the art after review of the following figures and description.

BRIEF DESCRIPTIONS OF THE DRAWINGS

For a better understanding of the embodiment(s) described herein and to show more clearly how the embodiment(s) may be carried into effect, reference will now be made, by way of example only, to the accompanying drawings in which.

Figure 1:
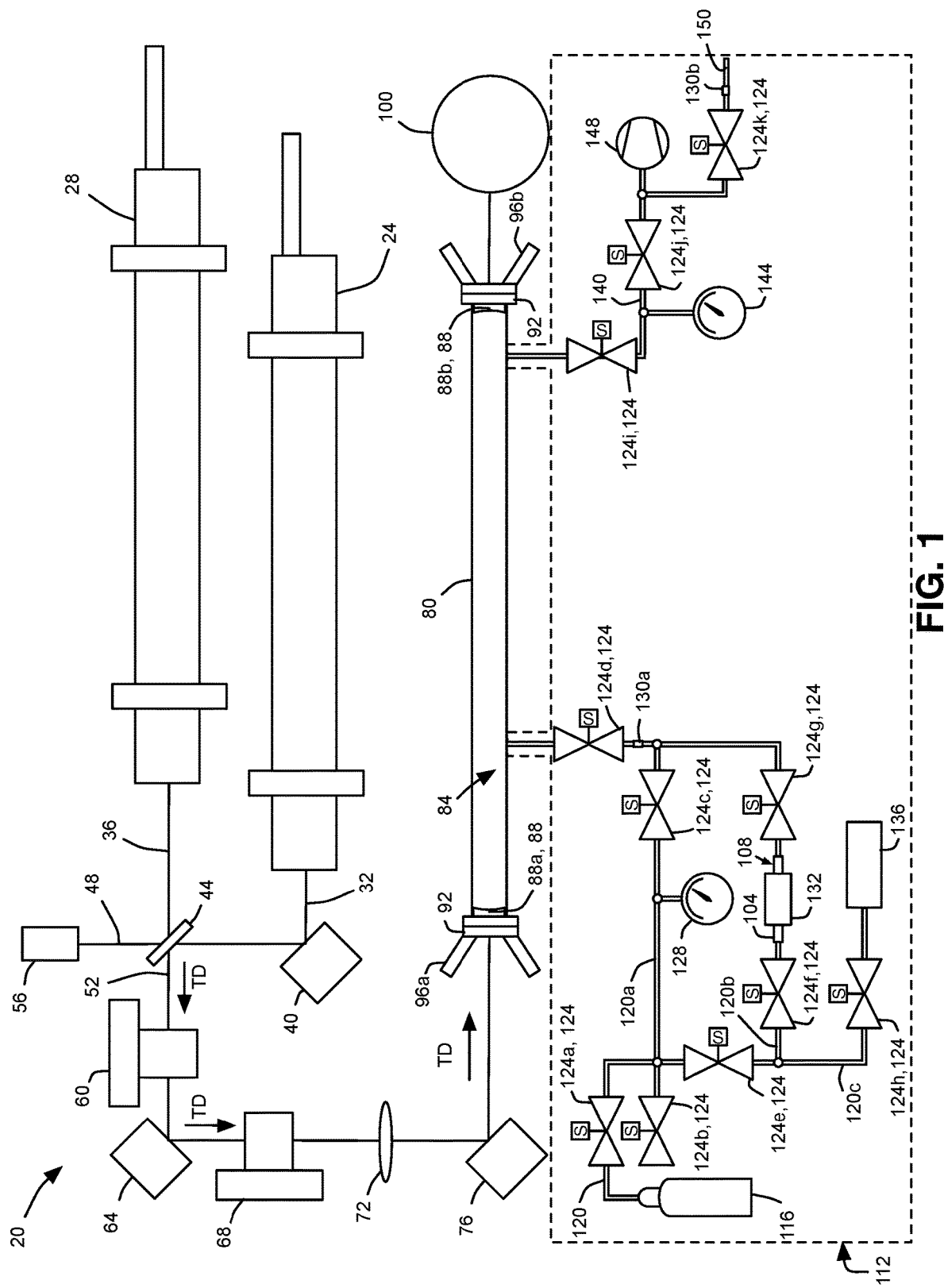
FIG. 1 is a schematic diagram of various optical and pneumatic components of a cavity ring-down spectroscopy system in accordance with one embodiment.

Unless otherwise specifically noted, articles depicted in the drawings are not necessarily drawn to scale.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiment or embodiments described herein. However, it will be understood by those of ordinary skill in the art that the embodiments described herein may be practiced without these specific details. In other instances, well-known methods, procedures and components have not been described in detail so as not to obscure the embodiments described herein. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Various components of a CRDS system 20 in accordance with a particular embodiment are shown in FIG. 1. A $CO_2$ laser 24 and a carbon-13 $O_2$ laser 28 are provided. The $CO_2$ laser 24 and the carbon-13 $O_2$ laser 28 are gas tube lasers that emit at a series of quasi-evenly-spaced, well-known frequencies that can be rapidly selected using an adjustable diffraction grating apparatus. Gas tube laser technology has a long history and is a stable and robust way of generating infrared radiation at precisely-known frequencies. Both the $CO_2$ laser 24 and the carbon-13 $O_2$ laser 28 emit light in the mid-IR spectrum.

Each of the $CO_2$ laser 24 and the carbon-13 $O_2$ laser 28 has an actuator and an output coupler that enable adjustment of the length of the laser cavity as well as an actuator to change the angle of grating at the back of the cavity, thereby changing its pitch to adjust which wavelengths it reflects. By both adjusting the length of the laser cavity and changing the angle of the grating, the laser can be very accurately tuned to a specific wavelength and desired mode quality.

The $CO_2$ laser 24 produces a first laser beam 32, and the carbon-13 $O_2$ laser 28 produces a second laser beam 36. Depending on the light frequency desired, either the $CO_2$ laser 24 is tuned and generates the first laser beam 32 while the carbon-13 $O_2$ laser 28 is detuned, or the carbon-13 $O_2$ laser 28 is tuned and generates the second laser beam 36 while the $CO_2$ laser 24 is detuned. In this manner, at most only one of the $CO_2$ laser 24 and the carbon-13 $O_2$ laser 28 outputs a beam at any particular time so that the first beam 32 and the second beam 36 are not combined simultaneously. Mid-infrared, and specifically long wavelength infrared, was chosen as the type of light as most volatile organic compounds absorb light in this range. As a result, multiple volatile organic compounds can be measured by a single system. $CO_2$ lasers operate in this range and have sufficient power and linewidth narrowness for ring-down spectroscopy. Using two lasers adds to the range and number of available wavelengths that the CRDS system 20 can use to analyze gaseous samples.

The first laser beam 32 is redirected via a mirror 40 on an optic mount towards a beam splitter 44. The beam splitter 44 is partially reflective and partially transmissive, and splits each of the first laser beam 32 and the second laser beam 36 into two beams, a sampling beam 48, and a working beam 52 that has the same characteristics as the sampling beam 48 and can be of similar intensity as the sampling beam 48.

The sampling beam 48 is received by a fast infrared detector 56. The fast infrared detector 56 measures the amplitude and the beat frequency of the sampling beam 48 using an oscilloscope. The beat frequency can indicate the presence of higher order modes resulting from a less-than-optimal tuning of the $CO_2$ laser 24 or the carbon-13 $O_2$ laser 28. In response to the detection of an undesirable beat frequency, the corresponding laser 24 or 28 is tuned until the amplitude of the beat frequency is minimized or eliminated while maximizing the intensity. If the amplitude of the beat frequency cannot be reduced below an acceptable level, the laser can be tuned to a different wavelength.

The working beam 52 continues to a first optical modulator 60, which then deflects the working beam 52 to a mirror 64 on an optic mount. The mirror 64 redirects the light towards a second optical modulator 68 that, in turn, deflects the working beam 52 to a focusing lens 72. The optical modulators are used to control the intensity of the light beam generated by the laser. In the present embodiment, the first and second optical modulators 60, 68 are acousto-optic modulators ("AOMs"), also referred to as Bragg cells. AOMs are one type of optical modulator that uses a piezoelectric transducer coupled to a material such as germanium or glass. In the described embodiment, the material is germanium. When an oscillating electric signal is applied to the piezoelectric transducer, the piezoelectric transducer vibrates, creating sound waves in the material. These sound waves expand and compress the material, thereby creating periodic variations in the refractive index and allowing for Bragg diffraction. Light entering the AOM at the first order Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively attenuating the light along the deflected optical path. A by-product of the AOM is that the frequency of the light being deflected is shifted.

In other embodiments, the optical modulators could alternatively be electro-optic modulators. An electro-optic modulator is another type of optical modulator that applies a DC or low-frequency electric field to a material to distort the position, orientation, and/or shape of the molecules of the material. As a result, the refractive index is altered to change the phase of the outgoing beam as a function of the applied field. By sending the beam through a polarizer, the phase modulation is converted to intensity modulation. In another method, a phase modulator when placed in a branch of an interferometer can act as an intensity modulator.

Further, while the CRDS system 20 is described as having two optical modulators, in other embodiments, the CRDS system can have fewer or a greater number of optical modulators.

The first and second optical modulators 60, 68 act as attenuators to adjust the intensity of the working beam 52 and extinguish the beam at the commencement of a ring-down event. A ring-down event includes the extinguishing of the working beam 52 illuminating a ring-down cavity or the detuning of the laser for the ring-down chamber, and the collection of light intensity data from the ring-down chamber. As they are AOMs, the first and second optical modulators 60, 68 use the acousto-optic effect to diffract the light using sound waves (normally at radio-frequency). In each of the first and second optical modulators, a piezoelectric transducer is coupled to a material such as germanium or glass, and an oscillating electric signal is used to cause the piezoelectric transducer to vibrate. The vibrating piezoelectric transducer creates sound waves in the material that expand and compress the material, thereby creating period variations in the refractive index and allowing for Bragg diffraction. Light entering the AOM at Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively extinguishing the light along the deflected optical path. Hence, the intensity of the sound can be used to modulate the intensity of the light in the deflected beam.

The intensity of the light deflected by each of the first and second optical modulators 60, 68 can be between about 85%, representing a maximum deflection efficiency of the optical modulators 60, 68, and an attenuation limit of each of the first and second optical modulators 60, 68 of about 0.1% of the input light intensity. When the acoustic wave applied to the germanium is turned off, the deflected beam loses about 30 dB, or 99.9%, of the previous intensity. The attenuation limit means the upper limit of how much of the input light intensity can be reduced by the optical modulator.

Optic modulators are asymmetrical in that, as a side effect, they Doppler-shift the frequency of light in a first mode when the input light is received at a first end thereof, and they Doppler-shift the frequency of light in a second mode that is counter to the first mode when the input light is received at a second end thereof and the attenuation power is the same. The Doppler shift of the frequency of the light is, however, in the same direction regardless of whether the light enters at a first end or at a second end.

Conventional CRDS systems use a single optical modulator and, as a result, have a working beam that is frequency shifted. These frequency shifts are generally small in relation to the frequency of the light, and can change the manner in which the light is absorbed by matter in the cavity, but this frequency shift can be compensated for during the analysis. If diffraction is towards the acoustic wave source of an AOM, the frequency shift is downwards, and if diffraction is away from the acoustic wave source, the frequency shift is upwards. As discussed, the effect is minimal.

The working beam 52 deflected by the second optical modulator 68 is focused via a focusing lens 72. As the laser beam, and thus the working beam 52, travels from the $CO_2$ laser 24 or the carbon-13 $O_2$ laser 28, it continues to diverge. The focusing lens 72 focuses the working beam 52 back down.

A mirror 76 on an optic mount thereafter redirects the working beam 52 towards a ring-down chamber 80. The two mirrors 64, 76 extend the length of the path of the working beam 52.

Figure 2:
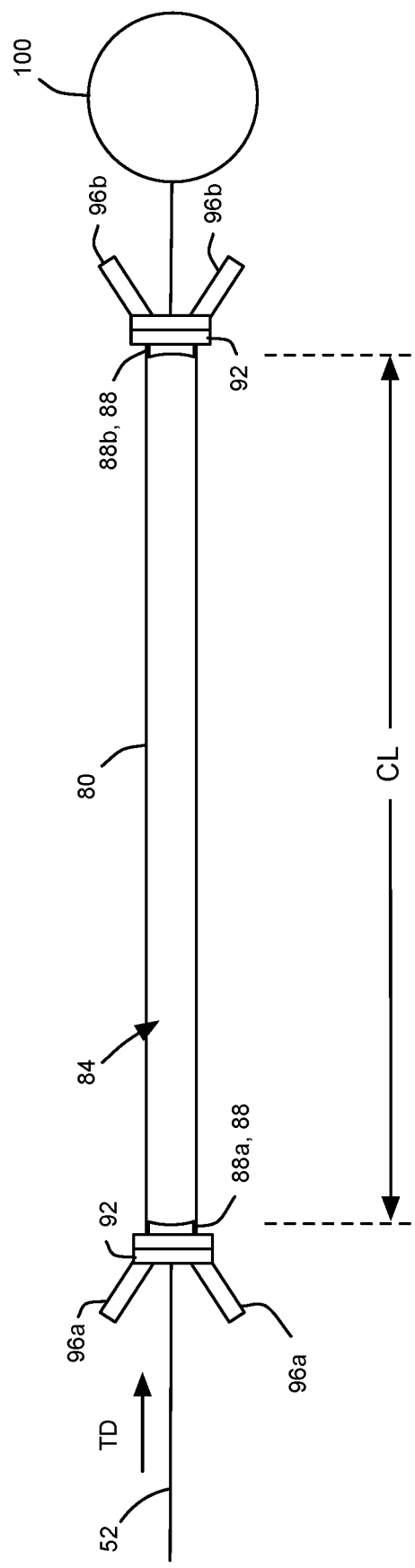
FIG. 2 is a schematic diagram of the ring-down cavity of the cavity ring-down spectroscopy system of FIG. 1.

Now referring to FIGS. 1 and 2, the ring-down chamber 80 is an elongated tube defining a resonant cavity referred to as a ring-down cavity 84 therein. A front cavity mirror 88a and a rear cavity mirror 88b (alternatively referred to herein as cavity mirrors 88) are positioned at longitudinal ends of the ring-down cavity 84. The cavity mirrors 88 are highly reflective, both to light directed to the cavity mirrors 88 from outside of the ring-down cavity 84 and directed to the cavity mirrors 88 within the ring-down cavity 84. As a result, a fraction of the working beam 52 is directed at the front cavity mirror 88a, about 0.1%, passes through the front cavity mirror 88a, and enters the ring-down cavity 84, and the majority of the working beam 52, about 99.9% is reflected back towards the mirror 76.

The cavity mirrors 88 are mounted on mirror mounts 92 that are actuatable to adjust the positioning and orientation of the cavity mirrors 88. In particular, the front cavity mirror 88a towards the front of the ring-down cavity 84 is mounted on a mirror mount 92 that is actuatable via three mechanized micrometers 96a. The rear cavity mirror 88b towards the rear of the ring-down cavity 84 is mounted on a mirror mount 92 that is actuatable via three piezoelectric micrometers 96b that can be manually adjusted for optical alignment or with a piezo that allows them to be adjusted further with the piezo driver.

The angle of each of cavity mirror 88 can be changed so that they are sufficiently aligned so that when a light beam enters the ring-down cavity 84, the light beam does not deviate. If one of the cavity mirrors 88 is askew, then some of the light gets reflected to the side of the ring-down cavity 84, intensity of the light is lost, high-order modes result, amongst other things. The micrometers 96 can also be simultaneously tuned to change the length of the ring-down cavity 84 without affecting the angle alignment. This allows for the tuning of the ring-down cavity 84 so that the ring-down cavity 84 resonates at the frequency of the light that is entering the ring-down cavity 84.

The focusing lens 72 focuses the laser light to match the optical mode of the ring-down cavity 84, so that the minimum waist of the beam is positioned at the same place as the minimum beam waist of the ring-down cavity 84. The position of the focusing lens 72 can be adjusted to match the optical mode of a range of laser wavelengths.

A light sensor in the form of a liquid nitrogen-cooled detector 100 is positioned behind the rear cavity mirror 88b to receive light escaping through it. The liquid nitrogen-cooled detector 100 measures the intensity of the light that escapes the ring-down cavity 84. Other types of sensors for measuring the intensity of the escaping light can be used in place of the liquid nitrogen-cooled detector 100.

Gaseous samples are loaded into the ring-down cavity 84 from a thermal desorption tube 104 that is used to collect the gaseous samples for testing. Thermal desorption tubes are generally made of stainless steel and contain various types of solid adsorbent material. The solid sorbents are selected for sampling specific compounds to trap and retain the compounds of interest even in the presence of other compounds, and allow the collected compounds to be easily desorbed or extracted for analysis. In addition, the solid sorbents which are selected do not react with the compounds of interest.

In a particular example, the gaseous samples are human breath samples collected from patients. A receiving end 108 of the thermal desorption tube 104 receives human breath collected from a human for testing. As a result, compounds of interest are more concentrated towards the receiving end 108 of the thermal desorption tube 104.

A pneumatic system 112 is used to load gaseous samples from thermal desorption tubes 104 into the ring-down cavity 84, and evacuate the pneumatic system 112, including the ring-down cavity 84. During loading of a gaseous sample, the pneumatic system 112 fills the ring-down cavity 84 with the gaseous sample that has been collected (i.e., to desorb the gaseous sample from the thermal desorption tube 104, get the gaseous sample into the ring-down cavity 84 without introducing contaminants), brings the pressure and temperature in the ring-down cavity to one atmosphere and 50 degrees Celsius, and seals the ring-down cavity 84. In this embodiment, the absorption spectra for a set of samples to which the measured absorption spectra are compared are determined at this pressure and temperature to ensure consistency between these parameters which can affect the results. In other embodiments, however, the pressure and temperature can be fixed at other levels for the known and measured absorption spectra. During evacuation of a gaseous sample, the pneumatic system 112 cleans the previously provided gaseous sample from the ring-down cavity 84 and the various conduits for guiding gaseous samples from the thermal desorption tube 104 to the ring-down cavity 84.

The pneumatic system 112 has an intake portion that includes a nitrogen gas source 116. The nitrogen gas source 116 is a supply of very clean nitrogen gas that is pressurized or that can pressurize the nitrogen gas to at least above one atmosphere of pressure. In the present embodiment, the nitrogen gas source 116 is pressurized at five psi above ambient pressure, but can be varied as long as the compression is sufficient to pressurize the ring-down cavity 84 to one atmosphere, or some other selected atmospheric pressure at which the analyses are run. In the illustrated embodiment, the nitrogen gas source 116 is the nitrogen gas that evaporates off a liquid nitrogen reservoir. The nitrogen gas source 116 is connected via conduit 120 to a gas inlet valve 124a. An auxiliary gas inlet valve 124b enables connection of other gases, but is not regularly employed. The gas inlet and auxiliary gas inlet valves 124a, 124b are in communication with a gas intake line 120a. A pressure meter 128 is positioned along the gas intake line 120a, as well as a gas intake line valve 124c. A filter 130a is positioned along the gas intake line 120a in front of a cavity inlet valve 124d that seals the gas intake line 120a from the ring-down cavity 84. The filter 130a inhibits the entry of contaminants into the ring-down cavity 84 where they can deposit on the cavity mirrors 88 and interfere with reflection.

The gas inlet and auxiliary gas inlet valves 124a, 124b are in communication with a pathing valve 124e. The pathing valve 124e enables or disables direct access to a desorption tube line 120b and a sample outlet line 120c.

The desorption tube line 120b includes a forward valve 124f and a rearward valve 124g. The thermal desorption tube 104 is positioned between the forward valve 124f and the rearward valve 124g, with the receiving end 108 of the thermal desorption tube 104 being positioned towards the rearward valve 124g. The thermal desorption tube 104 is positioned within a heater 132.

The sample outlet line 120c includes a sample outlet valve 124h and a mass flow controller 136.

The pneumatic system 112 also has an outlet portion that includes a cavity outlet valve 124i in communication with the ring-down cavity 84. An outlet line 140 is in communication with the cavity outlet valve 124i. A pressure meter 144 is positioned along the outlet line 140. A vacuum cutoff valve 124j is positioned between the pressure meter 144 and a vacuum pump 148. A vacuum intake valve 124k is in communication with the vacuum pump 148 and draws air through a pump intake line 150. A filter 130b is positioned in the pump intake line 150 to inhibit entry of contaminants that can interfere with the working of the vacuum pump 148.

Valves 124a to 124k may be alternatively referred to herein as valves 124.

While the cavity inlet valve 124d and the cavity outlet valve 124i are shown for convenience coupled to the ring-down cavity 84 at certain locations, it will be understood that the locations at which the valves 124d, 124i are coupled to the ring-down cavity 84 may vary. In a preferred configuration, the cavity inlet valve 124d is in communication with the ring-down cavity 84 towards an end thereof adjacent the front cavity mirror 88a and the cavity outlet valve 124i is in communication with the ring-down cavity 84 towards an end thereof adjacent the rear cavity mirror 88b.

When a new gaseous sample is to be loaded into the ring-down cavity 84, the thermal desorption tube 104 containing the new gaseous sample is coupled to the pneumatic system 112 as shown in FIG. 1.

During an evacuation phase, the vacuum intake valve 124k is opened and the vacuum pump 148 is turned on. The vacuum intake valve 124k is then closed, and the vacuum cutoff valve 124j, the cavity outlet valve 124i, the cavity inlet valve 124d, the gas intake line valve 124c, and the pathing valve 124e are opened in succession. The contents of the lines along this path and the ring-down cavity 84 are evacuated from the CRDS system 20 by the vacuum pump 148. The pressure meter 144 enables the determination of when the system has been evacuated sufficiently, especially when the pressure meter 128 is cut off from the vacuum pump 148. When it is determined that the system has been evacuated sufficiently, these same open valves 124j, 124i, 124d, 124c, and 124e are then closed in the reverse order. Thereafter, during a nitrogen fill phase, valves 124a, 124c, 124d, 124i, and 124j are opened to allow nitrogen gas from the nitrogen gas source 116 to fill the lines 120a and 140. The nitrogen gas is then purged using another evacuation phase. The nitrogen fill phase and the evacuation phase can be repeated as desired to clear out the lines. The CRDS system 20 is thus evacuated of the previously tested gaseous sample.

During the loading of the new sample, the thermal desorption tube 104 is flushed to remove carbon dioxide and water out of the thermal desorption tube 104 so that the amount of carbon dioxide and water loaded into the ring-down cavity 84 is minimized. In order to flush the thermal desorption tube 104, the gas intake valve 124a, the gas intake line valve 124c, and the rearward valve 124g are opened to give a path to the nitrogen gas to forward flush the thermal desorption tube 104. The thermal desorption tube 104 is selected to inhibit the collection of carbon dioxide and water with the gaseous sample, but there is still typically some carbon dioxide and water in the thermal desorption tube 104.

500 ml of nitrogen gas is put through the thermal desorption tube to get out carbon dioxide and water that have remained in the thermal desorption tube 104 from the original sample. Then the forward valve 124f and the sample outlet valve 124h are opened to provide a path to the mass flow controller 136. The mass flow controller 136 allows the nitrogen gas and borne carbon dioxide and water to be released at a specified flow rate. In the present configuration, this flow rate is 500 ml/min. All the valves 124 are then closed.

Once the carbon dioxide and the water have been removed from the thermal desorption tube 104, the pneumatic system 112 is evacuated again using the same process discussed above to remove the nitrogen gas just introduced in the pneumatic system 112 lines. The heater 132 surrounding the thermal desorption tube 104 then heats the thermal desorption tube 104 to the desired temperature to thermally desorb the new sample within the thermal desorption tube 104. The gas inlet valve 124a, the pathing valve 124e, the forward valve 124f, the rearward valve 124g, and the cavity inlet valve 124d are then opened to provide a direct path for the nitrogen gas from the nitrogen gas source 116, through the thermal desorption tube 104 having desorbed compounds of interest, and to the ring-down cavity 84.

It is desired to achieve a pressure of one atmosphere within the ring-down cavity 84 as all of the reference data collected and analyzed is at this pressure level, thereby ensuring that the results are repeatable.

The gas inlet valve 124a is toggled open and closed by the system, then the system waits for the pressure reading at the pressure meter 128 to stabilize and reach one atmosphere. If, upon stabilization of the pressure meter 128, the pressure reading is still below one atmosphere, the gas inlet valve 124a is toggled again to repeat the process until the pressure reading is one atmosphere. When the pressure meter 128 shows that the pressure level in the ring-down cavity 84 is one atmosphere, the valves are all closed.

If it is desired to desorb at multiple temperatures, the vacuum pump 148 is turned on, the cavity outlet valve 124i and the vacuum cutoff valve 124j are opened to evacuate the ring-down cavity 84. Then the cavity outlet valve 124i is closed before the desorption process is repeated.

A full evacuation is generally not performed between multiple desorptions as there is still some of the gaseous sample between the rearward valve 124g and the cavity inlet valve 124d that would be otherwise lost.

By pressurizing a fixed volume ring-down cavity containing the gaseous sample to a desired pressure level in this manner, the surface area within the ring-down cavity to which compounds can adhere can be decreased in comparison to variable volume ring-down cavities that may be used to raise the pressure within the cavity to the desired level.

Further, the pressure meter 128 is upstream from the path of the gaseous sample from the thermal desorption tube 104 to the ring-down cavity 84, thereby preventing its contamination by the sample.

Figure 3:
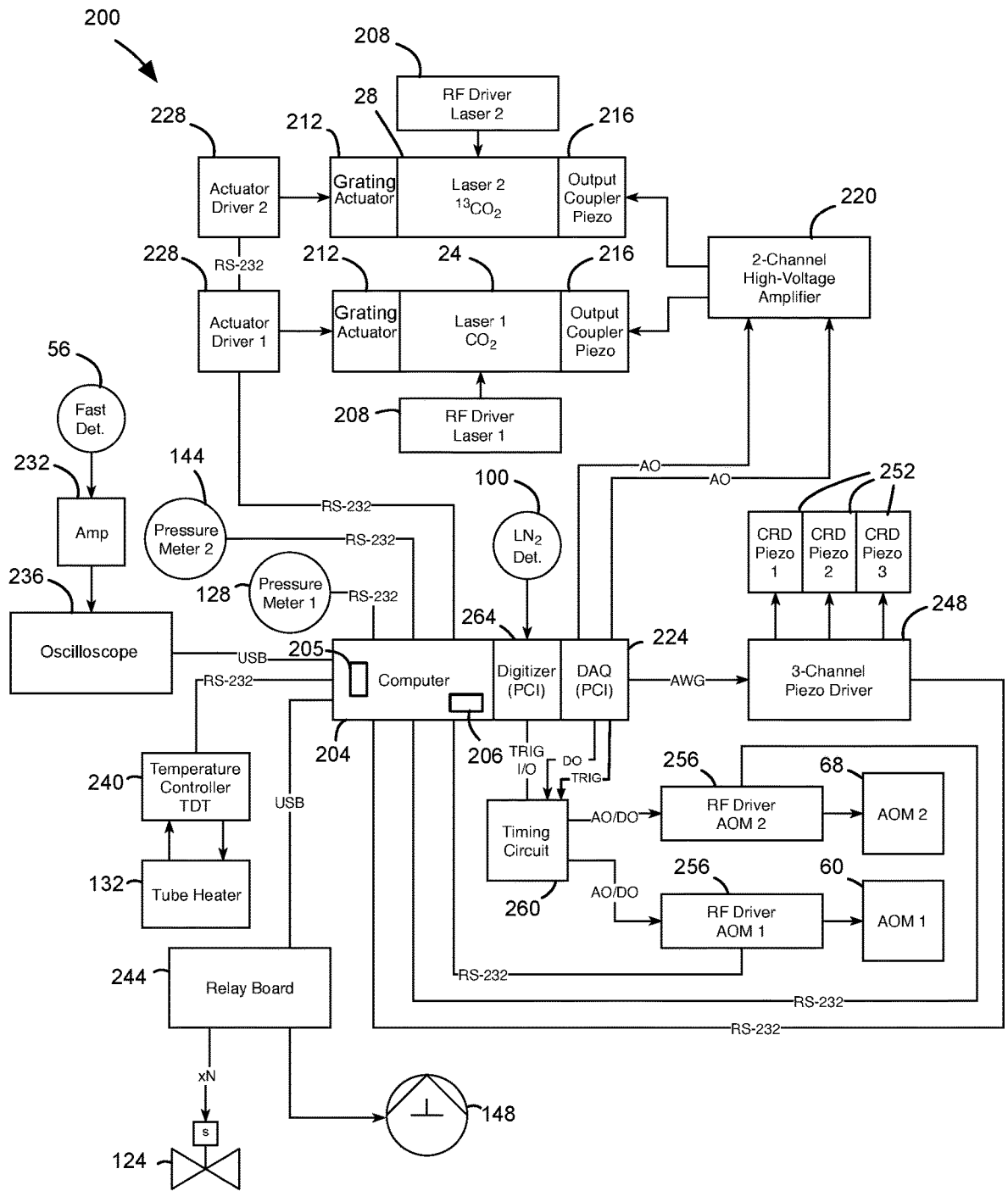
FIG. 3 is a schematic diagram of an electrical control system for controlling the various optical and pneumatic components of the cavity ring-down cavity ring-down system shown in FIGS. 1 and 2.

FIG. 3 is a schematic diagram of an electronic control subsystem 200 for various components of the CRDS system 20 that are also illustrated. All of the lines represent electrical or electronic signals, with arrows representing unidirectional communications, setting of a voltage, etc., and lines that are not arrows representing bidirectional communications.

A computer 204 including one or more processors acts as a control module that controls the function of the various components illustrated in FIGS. 1 and 2. The computer 204 has one or more processors 205 and storage 206 storing computer-executable instructions that, when executed by the processor 205, cause the processor 205 to direct the other components of the CRDS system 20 as described herein.

A pair of RF drivers 208 send approximately 40 MHz signal to power the $CO_2$ laser 24 and the carbon-13 $O_2$ laser 28. Each of the lasers 24, 28 is tuned using an output coupler and a diffraction grating. A grating actuator 212 actuates (turns) the diffraction grating. Another actuator actuates (translates) the output coupler. Each output coupler is driven by a 1000V output coupler piezo 216. A two-channel high-voltage amplifier 220 that powers the output coupler piezos 216 is adjustable between 0V and 1000V. The high-voltage amplifier 220 is set with an analog output signal from a data acquisition ("DAQ") card 224 in the computer 204. The DAQ generates output between 0V and 10V, and the high-voltage amplifier 220 multiplies the signal by 100 to generate a signal of 0V to 1000V to power the output coupler piezo 216. Each grating actuator 212 that changes the angle for the grating is driven by an actuator driver 228 that is given instructions by the computer 204 via RS-232. Each grating actuator 212 is moved so many millimeters, which is translated into a pitch angle of the laser 24, 28.

Data signals from the pressure meters 128, 144 of the pneumatic system 112 are received through RS-232.

The fast infrared detector 56 is connected to a small amplifier 232 and an oscilloscope 236 that can be used to read the amplitude and frequency of the beat signal that is used to tune the lasers 24, 28.

A temperature controller 240 for the thermal desorption tube heater 132 is controlled via RS-232 by the computer 204. The tube heater 132 includes a temperature sensor and a piece of aluminum that has heating tape wrapped around it. The heating tape and the temperature sensor are both connected to the temperature controller 240 which is a PID (proportional integral derivative) controller. The controller sets and reads back the temperature via RS-232 to the main computer 204.

A relay board 244 is connected to the computer 204 and is used to turn on and off all of the solenoid valves 124 and the vacuum pump 148.

A three-channel piezo driver 248 drives piezo actuators 252 that actuate the micrometers 96b to adjust the length of the ring-down cavity 84. Each channel has two components: communications to the piezo driver through RS-232, and analog input from the DAQ card 224. In other embodiments, two or more piezo drivers can be employed.

Each optical modulator 60, 68 is driven with an RF driver 256 that sends approximately a 40 MHz signal. Changing the frequency of the RF driver 256 changes the Bragg angle for a given optical wavelength, or changes the optical wavelength that a given or fixed Bragg angle is attuned to. If the RF driver 256 is tuned to a specific frequency and set to full power, most of the working beam 52 (about 85%) gets through. If adjusted to 80%, 70%, then the optical modulator 60, 68 will attenuate. If the RF driver 256 is set to zero, the optical modulator 60, 68 shuts off completely. The frequency of the RF driver is set through a component via RS232. An analog and digital component can set the amplitude and the on/off condition of the RF driver 256. In particular, the DAQ card 224 sends a signal to the timing circuit 260 which, in turn, generates the four necessary signals needed to enable and set the amplitude of the RF drivers. The timing circuit 260 can operate in a steady state condition or a ring-down triggering condition where the timing circuit 260 sets the four voltages to zero, and then returns to the previous voltage level after a pre-determined amount of time.

There is a digital output ("DO") from the DAQ card 224 that controls the timing circuit 260.

Referring now to FIGS. 1 and 3, once the gaseous sample is loaded in the ring-down cavity 84, one laser 24, 28 is tuned to a specific wavelength and its light is directed through the first optical modulator 60, reflected by the mirror 64, through the second optical modulator 68, and reflected by the mirror 72 to the ring-down chamber 80. The optical modulators 60, 68 attenuate the working beam 52 somewhat to modulate its intensity.

When the working beam 52 reaches the front cavity mirror 88a, a fraction, about 0.1%, penetrates the front cavity mirror 88a to enter the ring-down cavity 84. The majority of the working beam, about 99.9%, is initially reflected back along the same path to the working laser 24 or 28.

Initially, the ring-down cavity 84 is not illuminated. Light enters the ring-down cavity 84 and, as the majority of the light in the ring-down cavity 84 is reflected between the two cavity mirrors 88, the amount, or power, of light in the ring-down cavity 84 starts increasing as further light is introduced from outside via the working beam 52. A certain fraction of the light leaks out past the cavity mirrors 88. It takes a duration of time to "fill" the ring-down cavity 84 with light, and this can occur when the cavity length CL is equal to an adjacent resonance length of the ring-down cavity 84 for the tuned laser. At that point, there is an equilibrium between the incoming light and the leakage. Once this equilibrium is achieved, the laser 24, 28 is extinguished or otherwise stopped from entering the ring-down cavity 84 via the optical modulators 60, 68. In other embodiments, the laser can be detuned so that it does not resonate for the configured cavity length.

Figure 4A:
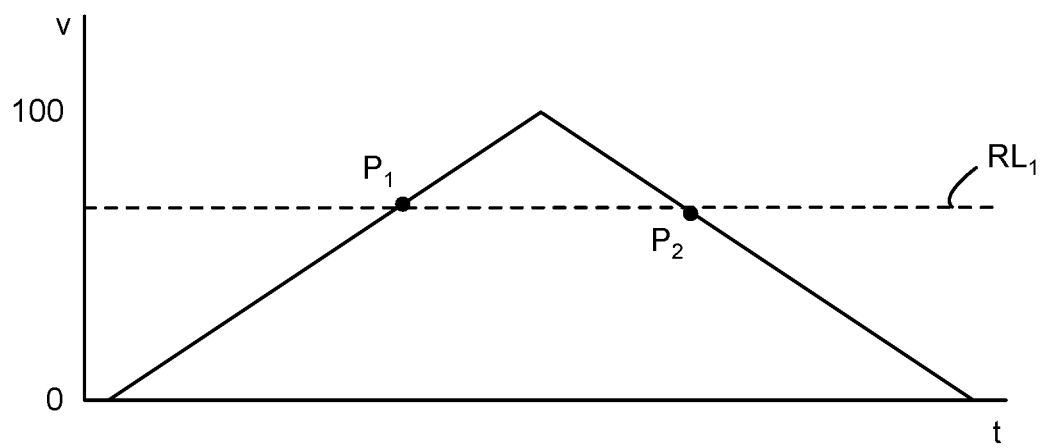
FIG. 4A shows a triangular waveform applied to a piezo driver to actuate a rear cavity mirror of the ring-down cavity of FIG. 2, wherein a single resonance point is traversed.

Now with reference to FIGS. 2 and 4A, one approach to locating an adjacent resonance length of the ring-down cavity 84 for the selected laser wavelength is shown. In the illustrated approach, the piezo driver 248 is controlled by the computer 204 to transmit to each of the piezo actuators 252 output commencing at 0 volts and gradually increasing to 100 volts, resulting in about 7.5 microns of movement of the rear cavity mirror 88b in the presently described configuration, then gradually decreasing back to 0 volts. The corresponding triangle wave is shown in FIG. 4A. In other embodiments, the range of voltages can be varied. As the voltage provided to the piezo actuators 252 is increased or decreased, the piezoelectric micrometers 96b move the rear cavity mirror 88b in a direction towards or away from the front cavity mirror 88a, thereby changing the cavity length CL of the ring-down cavity 84. The voltage that needs to be applied to the piezo actuators 252 to actuate the rear cavity mirror 88b so that the cavity length matches an adjacent resonance length is shown as and may be alternatively referred to hereinafter as an adjacent resonance length RL.

Figure 4B:
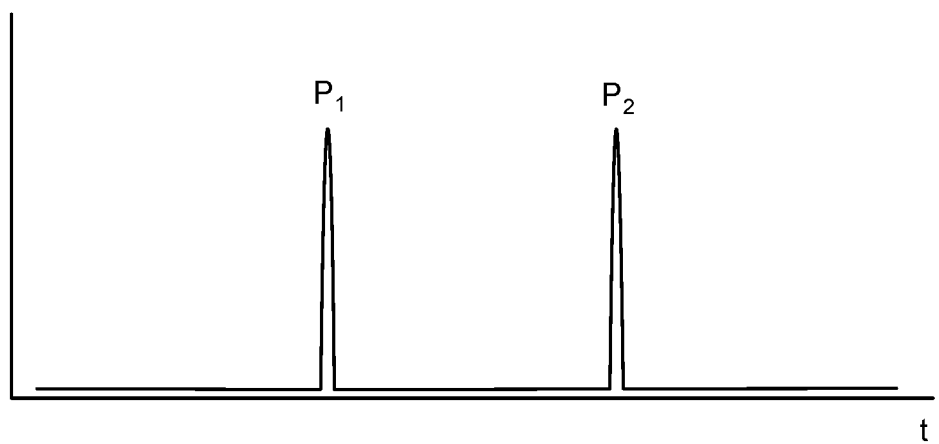
FIG. 4B shows the detected light intensity during application of the triangular waveform to the piezo driver driving actuation of the rear cavity mirror using the triangular waveform of FIG. 4A.
Figure 4C:
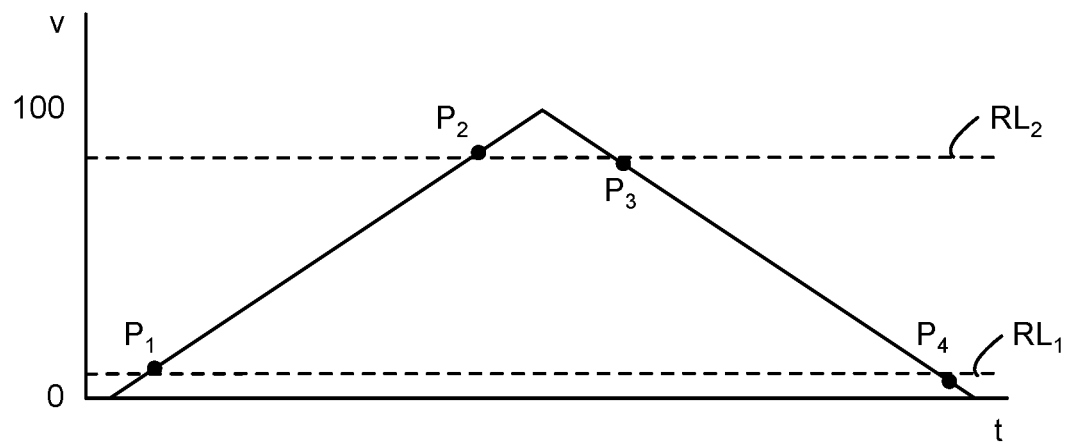
FIG. 4C shows the triangular waveform applied to the piezo driver to actuate the rear cavity mirror of the ring-down cavity of FIG. 3, wherein two resonance points are traversed.

As a result of the selected amplitude of this triangle wave and the configured wavelength of the laser light, the voltage at which the cavity length CL becomes equal to a resonance length RL either twice or four times, as shown in FIGS. 4A and 4C respectively, depending on the difference between the initial cavity length CL when zero voltage is applied to the piezo actuators 252 and a first of the resonance lengths $RL_1$ at the initial voltage.

When the ring-down cavity 84 is in resonance and approaches equilibrium (that is, the amount of light leaking out via the cavity mirrors 88 is equal to the amount of light entering from the working beam 52), there is destructive interference with the incoming laser light such that none or very little of the incoming laser light is reflected by the front cavity mirror 88a. As a result, once the ring-down cavity 84 is at equilibrium, reflection of the portion of the working beam 52 within the bandwidth of the ring-down cavity that is directed at the front cavity mirror 88a is substantially eliminated.

As shown in FIG. 4A, as the voltage is increased, the intensity of light detected by the liquid nitrogen-cooled detector 100 peaks at $P_1$, and as the voltage is decreased, the intensity of light detected by the liquid nitrogen-cooled detector 100 peaks at $P_2$. Of interest is that the voltage at which $P_1$ occurs is generally higher than the voltage at which $P_1$ occurs. For example, when the voltage is being increased, the light intensity peak may occur at 70, and when the voltage is being decreased, the light intensity peak may occur at 63 volts. This is likely as a result of hysteresis of the piezo actuators 252 of the piezoelectric micrometers 96b. The resultant light intensities detected by the liquid nitrogen-cooled detector 100 is shown in FIG. 4B.

Figure 4D:
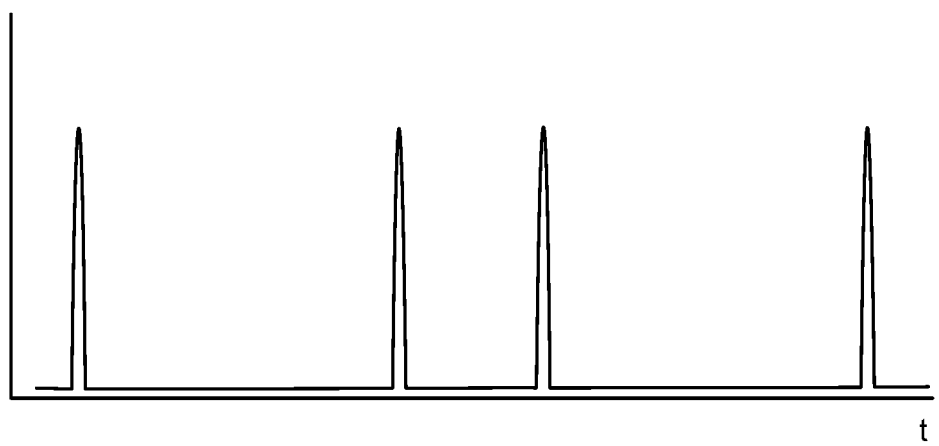
FIG. 4D shows the detected light intensity during application of the triangular waveform to the piezo driver driving actuation of the rear cavity mirror using the triangular waveform of FIG. 4C.

Similarly, as shown in FIG. 4C, as the voltage is increased, the intensity of light detected by the liquid nitrogen-cooled detector 100 peaks at $P_1$ and $P_2$, and as the voltage is decreased, the intensity of light detected by the liquid nitrogen-cooled detector 100 peaks at $P_3$ and $P_4$. The voltages at which $P_1$ and $P_2$ occur are generally higher than the voltage at which $P_3$ and $P_4$ occur. The resultant light intensities detected by the liquid nitrogen-cooled detector 100 is shown in FIG. 4D.

Figure 5:
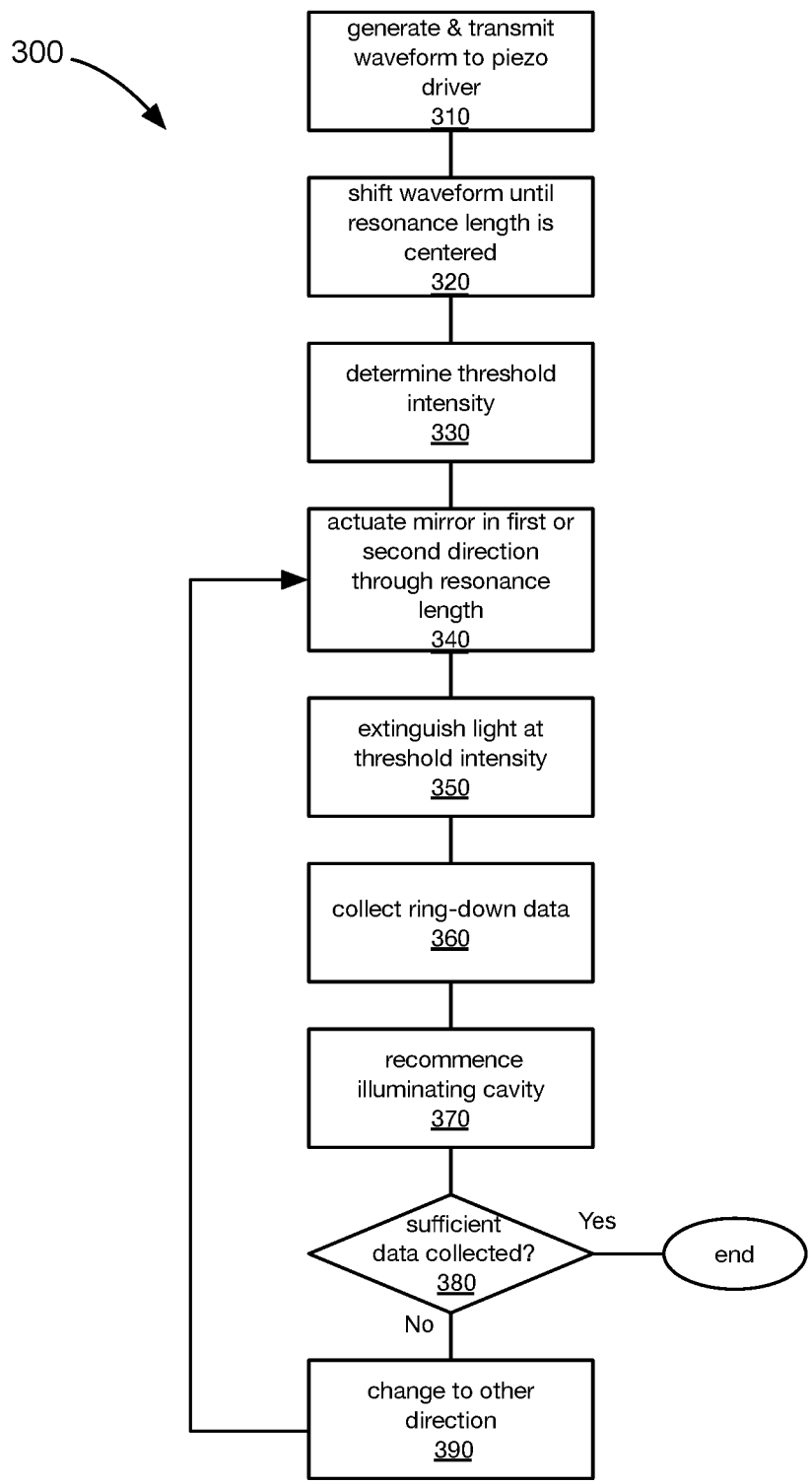
FIG. 5 shows the general method of calibrating and performing cavity ring-down events using the cavity ring-down spectroscopy system of FIG. 1.

A different method of tuning the ring-down cavity 84 and collecting cavity ring-downs was then developed, and is illustrated generally at 300 in FIG. 5. The method 300 commences with the generation of a sinusoidal waveform that is transmitted to the piezo driver 248 (310). The computer 204, via the digitizer 264, directs the DAQ 224 to generate and transmit a sinusoidal waveform to the piezo driver 248. The generated sinusoidal waveform voltage is an analog waveform generated from 30,000 points in this embodiment, but this number can be varied significantly. The sinusoidal waveform in the present embodiment has a frequency of about 200 Hz, and the sinusoidal waveform voltage has an amplitude of about two volts and an offset of two volts, but these can be varied in other embodiments. The sinusoidal waveform, which is digitally generated at 500,000 samples per second, is used to instruct the piezo driver 248 how to apply voltage to the piezo actuators 252. Thus, the piezo driver 248 applies a sinusoidal waveform voltage to the piezo actuators 252. Actuation of the rear cavity mirror 88b via a sinusoidal waveform voltage diminishes the occurrence of vibrations that can occur around sharp changes in velocity such as can occur at the peaks and troughs of a triangle waveform.

Figure 6A:
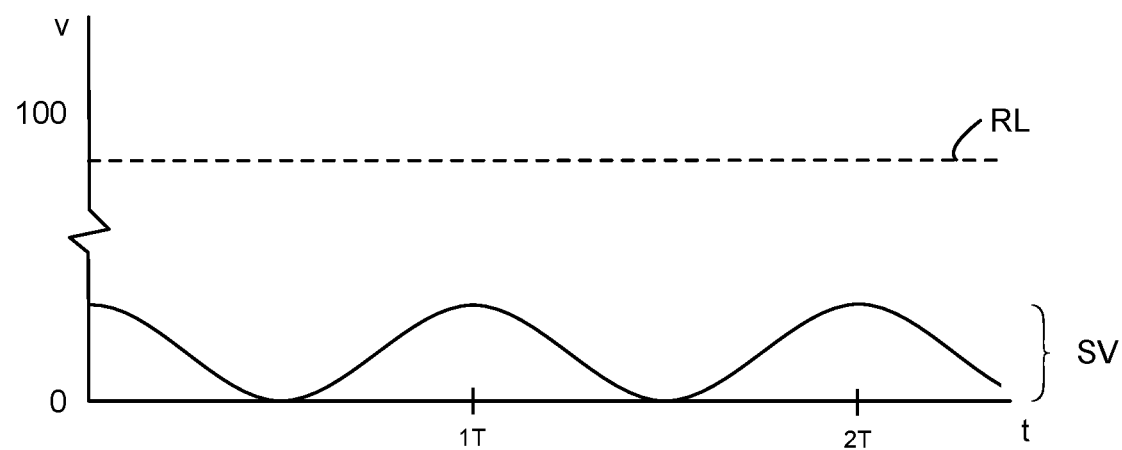
FIG. 6A shows a sinusoidal voltage applied to the piezo driver to actuate the rear cavity mirror of the ring-down cavity of FIG. 3, and a voltage level corresponding to a cavity resonance point.

FIG. 6A shows a sinusoidal waveform voltage SV generated by the piezo driver 248 in response to receiving the sinusoidal waveform from the DAQ 224. As can be seen, movement of the rear cavity mirror 88b via the sinusoidal waveform voltage SV does not cause adjustment of the cavity length CL via actuation of the rear cavity mirror 88b to match an adjacent resonance length RL of the ring-down cavity. The effective constant motion of the rear cavity mirror 88b allows the low resolution of the digital setting on the piezo to be overcome. There are enough points to provide a smooth motion of the piezo actuators 252 even though the points are discrete. In fact, the piezo actuators 252 have momentum as they are driven between points, thus enabling a much higher effective resolution.

Figure 6B:
FIG. 6B shows light intensity detected during actuation of the rear cavity mirror using the sinusoidal voltage of FIG. 6A.

FIG. 6B shows the resultant light intensity detected by the liquid nitrogen-cooled detector 100 as a result of movement of the rear cavity mirror 88b using the sinusoidal waveform SV of FIG. 6A. As the cavity length CL does not near the resonance length RL, destructive interference does not allow light intensity to build up in the ring-down cavity 84.

Referring back to FIG. 5, the sinusoidal waveform voltage SV is then shifted until an adjacent resonance length RL is centered in the sinusoidal waveform voltage SV (320). The computer 204 directs the piezo driver 248 via a digital signal sent via RS-232 to add a base voltage to the sinusoidal waveform voltage and increases it until a laser light intensity peak is detected by the liquid nitrogen-cooled detector 100. The liquid nitrogen-cooled detector 100 reports the detected light intensity levels to the digitizer 264 and thus the computer 204, thereby creating a feedback loop. By adding the sinusoidal waveform voltage that effectively emulates a continuous curve to the digital base voltage, much higher resolution is achieved at higher voltages.

Figure 6C:
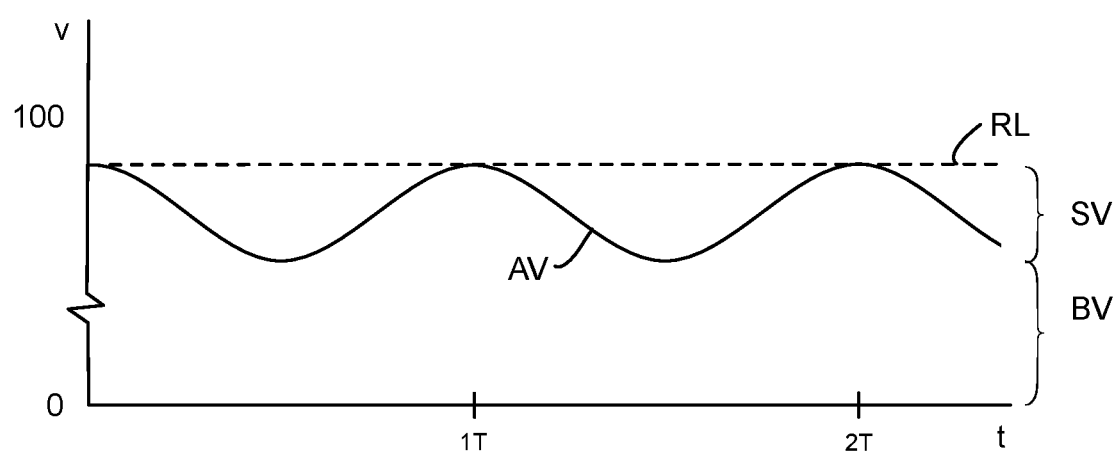
FIG. 6C shows the sinusoidal voltage of FIG. 6A after shifting of the sinusoidal voltage upwards until its peaks achieve the voltage level corresponding to the cavity resonance point.

FIG. 6C shows the base voltage BV having been added to the sinusoidal waveform voltage SV to generate an aggregate voltage AV. The aggregate voltage AV moves the rear cavity mirror 88b through and back again through a position at which the cavity length CL between the front cavity mirror 88a and the rear cavity mirror 88b is equal to an adjacent resonating length RL of the ring-down cavity 84.

Figure 6D:
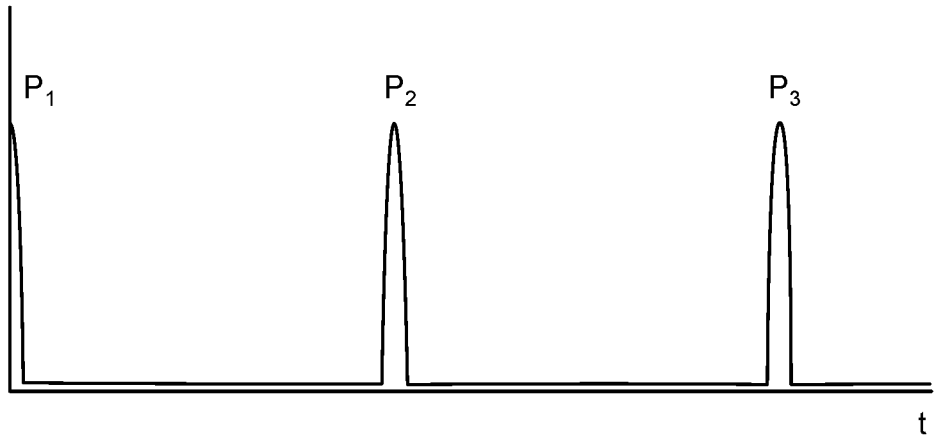
FIG. 6D shows light intensity detected during actuation of the rear cavity mirror using the sinusoidal voltage of FIG. 6C.

FIG. 6D shows the corresponding light intensity detected and reported back by the liquid nitrogen-cooled detector 100 as the aggregate voltage AV is applied to the piezo driver 248 as shown in FIG. 6C. The light intensity at times at which the cavity length CL matches the resonating length RL peaks, as shown at peaks $P_1$, $P_2$, and $P_3$, and in between these events is generally deemed noise.

Figure 6E:
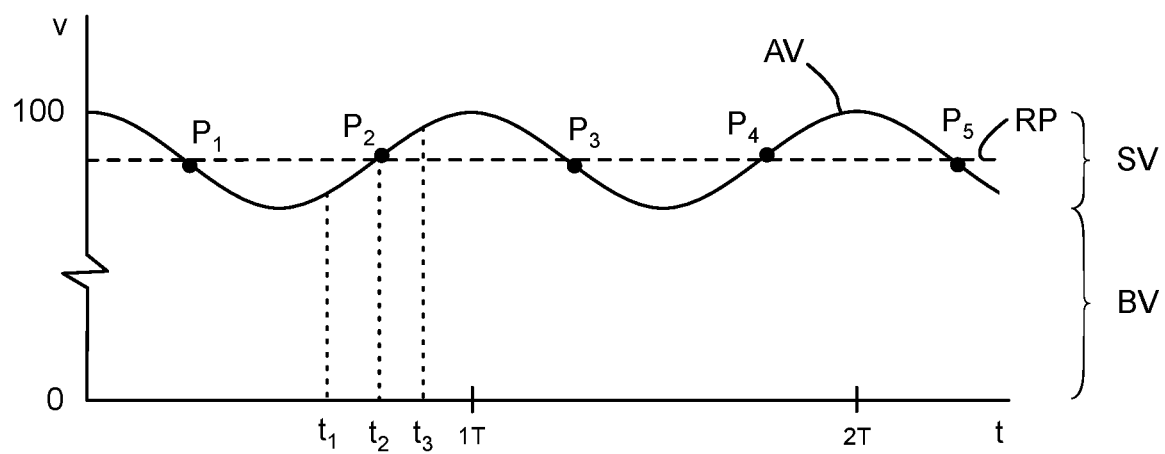
FIG. 6E shows the sinusoidal voltage of FIGS. 6A and 6C after shifting of the sinusoidal voltage upwards until the voltage level corresponding to the cavity resonance point is centered in the voltage range of the sinusoidal waveform.

The computer 204 continues to increase the base voltage BV via RS-232 until the light intensity peaks detected by the liquid nitrogen-cooled detector 100 are equally spaced apart time-wise by a half-period T/2, as shown in FIG. 6E. When the light intensity peaks are equally spaced apart, the resonance length RL is matched by the cavity length CL halfway between the minimum and maximum values of the aggregate voltage AV. While the base voltage BV is being adjusted, fluctuations in the voltage corresponding to the adjacent resonance length RL are monitored. During the initialization process, the voltage corresponding to the adjacent resonance length RL can fluctuate, possibly at least partially as a result of the "warming up" of components. This voltage generally settles after a short time. The shifting of the sinusoidal waveform voltage SV to center the voltage corresponding to the adjacent resonance length in the sinusoidal waveform voltage SV is only completed once the voltage corresponding to the adjacent resonance length RL is deemed to have settled.

Figure 6F:
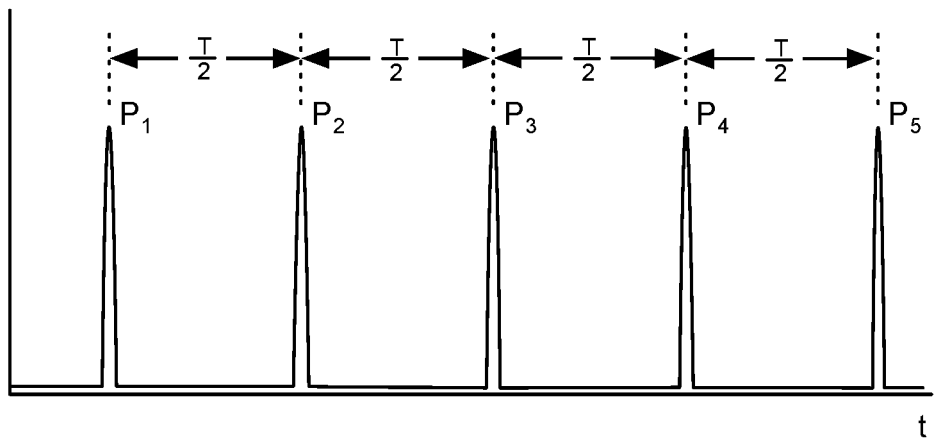
FIG. 6F shows light intensity detected during actuation of the rear cavity mirror using the sinusoidal voltage of FIG. 6E, wherein peak intensities occur every half period.

FIG. 6F shows the light intensity detected by the liquid nitrogen-cooled detector 100 corresponding to the aggregate voltage AV applied to the piezo driver 248 as shown in FIG. 6E. As can be seen, the peaks $P_1$ to $P_5$ are spaced apart equally and separated by one half of the period, or T/2, of the sinusoidal waveform voltage SV, equal to 15,000 points of the digitizer 264.

Figure 7A:
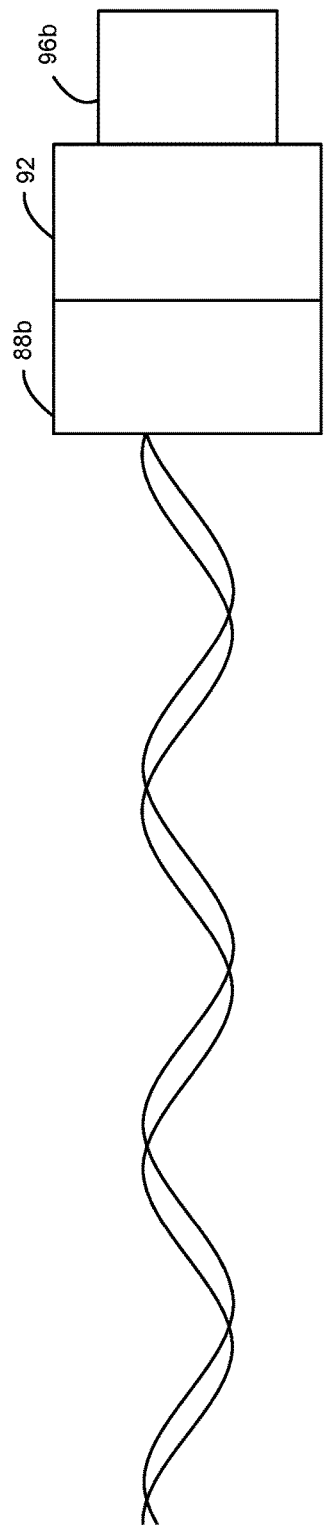
FIGS. 7A to 7C show three positions of the rear cavity mirror at times $t_1$, $t_2$, and $t_3$ and the corresponding reflected light waves.
Figure 7B:
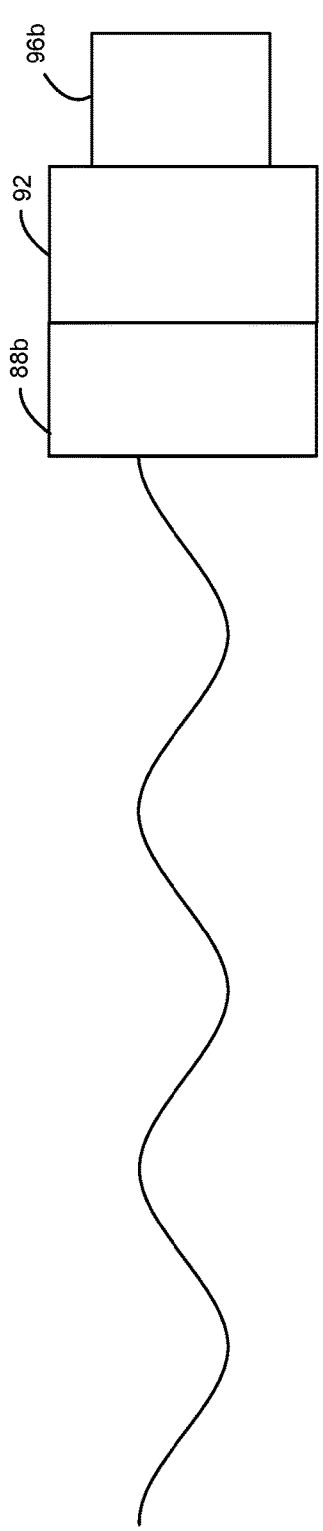
Figure 7C:
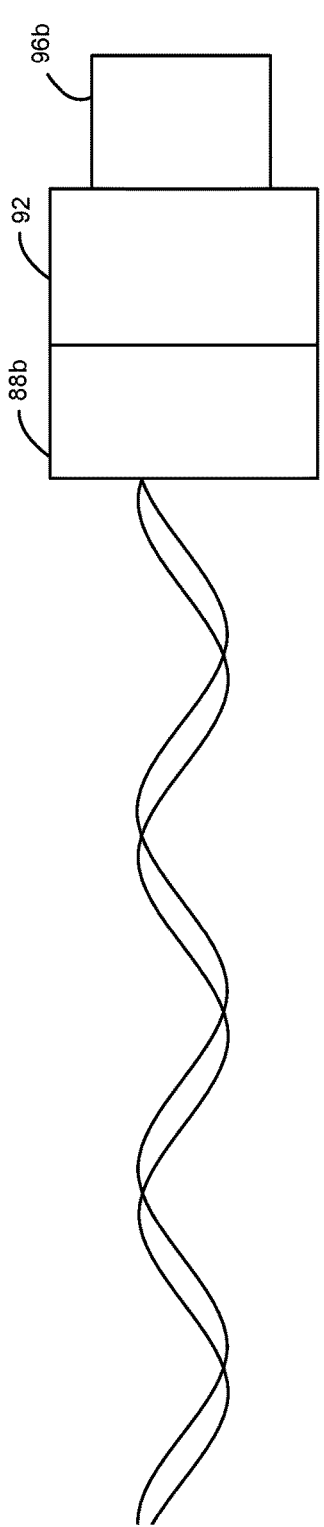

FIGS. 7A to 7C show the destructive or constructive interference of the laser light in the ring-down cavity 84 at times $t_1$, $t_2$, and $t_3$ shown in FIG. 6E respectively. In particular, in FIG. 7A, the cavity length CL is being shortened through the increasing of the voltage applied to the piezo driver 264, and thus movement of the rear cavity mirror 88*b* towards the front cavity mirror 88*a*, but is longer than an adjacent resonance length RL of the ring-down cavity 84. As a result, the light reflecting off of the rear cavity mirror 88*b* is out of phase with the light approaching the rear cavity mirror 88*b*, resulting in destructive interference. As the light is subsequently reflected between the front and rear cavity mirrors 88*a*, 88*b*, the destructive interference negates the intensity of the light.

In FIG. 7B, the cavity length CL is still being shortened through the increasing of the voltage applied to the piezo driver 264, and is equal to the resonance length RL of the ring-down cavity 84. As a result, the light reflecting off of the rear cavity mirror 88*b* is in phase with the light approaching the rear cavity mirror 88*b*, resulting in constructive interference, thereby intensifying the light in the ring-down cavity 84. At this position, the rear cavity mirror 88*b* is continually being actuated towards the front cavity mirror 88*a* and, thus passes through the position at which the cavity length is equal to the adjacent resonance length effectively without stopping.

In FIG. 7C, the cavity length CL is still being shortened through the increasing of the voltage applied to the piezo driver 264, but is shorter than the adjacent resonance length RL of the ring-down cavity 84. Here, the rear cavity mirror 88*b* continuously travels towards the front cavity mirror 88*a*. As a result, the light reflecting off of the rear cavity mirror 88*b* is out of phase with the light approaching the rear cavity mirror 88*b*, resulting in destructive interference. As the light is subsequently reflected between the front and rear cavity mirrors 88*a*, 88*b*, the destructive interference negates the intensity of the light.

Referring again to FIG. 5, once the voltage corresponding with the resonance length RL is centered in the range of the aggregate voltage AV, the computer determines the threshold light intensity (330). In this embodiment, the threshold light intensity is set to 90% of the peak light intensity empirically to enable time for the laser light to be extinguished, as the electronic components have a delay. The light intensity is received from the liquid nitrogen-cooled detector 100.

The computer 204 then continues to actuate the rear cavity mirror 88*b* using the aggregate voltage AV shown in FIG. 6E. In particular, the computer 204 directs the piezo driver 248 to generate a base voltage BV, and controls the DAQ 224 to provide the piezo driver 248 with the sinusoidal waveform used by the piezo driver 248 to generate a sinusoidal waveform voltage SV that is added to the base voltage BV to arrive at the aggregate voltage AV. The aggregate voltage AV generated by the piezo driver 248 moves the rear cavity mirror 88*b* in a first or second direction through a position at which the cavity length CL is equal to the resonance length RL (340).

Upon detection of the threshold intensity previously determined, the digitizer 264 sends a trigger pulse to the timing circuit 260 to cause the optical modulators 60, 68 to extinguish the laser light provided to the ring-down cavity 84 (350). In particular, the digitizer 264 triggers the timing circuit 260 to set the RF driver voltages to zero.

The timing circuit 260 simultaneously directs the first and second optical modulators 60, 68 to attenuate the light beam at or close to an attenuation limits of the optical modulators 60, 68 to reduce an intensity of the light beam from the first optical modulator 60. In the CRDS system 20, by directing both optical modulators 60, 68 to shut off simultaneously, the amount of light deflected by the first optical modulator 60 during the short span of time is markedly reduced by the second optical modulator 68 as it is shutting down.

The second optical modular 68 greatly increases the attenuation achieved via the first optical modulator 60 alone. In the currently described embodiment, if the first optical modulator 60 can attenuate by 30 dB, and the second optical modulator 68 can attenuate by an additional 30 dB, with the total attenuation achieved via the optical modulators 60, 68 being the sum of their attenuation, or 60 dB. During filling of the ring-down cavity 84 with light, the optical modulators 60, 68 attenuate the working beam 52 to modulate its intensity. In the present configuration, each of the optical modulators 60, 68 attenuate the working beam 52 by 5 dB, for a total attenuation of 10 dB. As a result, each of the optical modulators 60, 68 can still further attenuate the working beam 52 by 25 dB for a total further attenuation of 50 dB during the extinguishing of the working beam 52. In a conventional setup, one optical modulator would have to attenuate a working beam by 10 dB, leaving 20 dB of further attenuation available for extinguishing the working beam. As will be understood, the working beam 52 can be extinguished much more rapidly via 50 dB of further attenuation via the two optical modulators 60, 68 than with one optical modulator with 20 dB of further attenuation. As a result, the amount of additional light introduced into the ring-down cavity 84 after the optical modulators 60, 68 have been directed to shut down is a small fraction of the light further introduced by a single optical modulator setup in a conventional CRDS system. By extinguishing the working beam 52 more quickly, the measured decay of light in the ring-down cavity 84 is less affected by the additional light during the ramp-down times of the optical modulators 60, 68, thus granting higher precision when matching the observed decay times against known decay times.

Extinguishing of the laser light provided to the ring-down cavity 84 enables a ring-down event to be commenced. The resonating laser light provided to the ring-down cavity 84 can be extinguished in other manners in alternative embodiments, such as, for example, by detuning the laser. By initiating the triggering of a ring-down event via a threshold, the ring-down event can be timed to occur during the peak while the ring-down cavity 84 is in resonance with the laser light, and not on one side of the peak. Further, as the bandwidth of the resonance is about 10 millivolts, the resolution of the piezo driver 248 is insufficiently granular to properly track the peak.

During the ring-down event, the computer 204 registers the light intensity data reported by the liquid nitrogen-cooled detector 100 exiting from the back end of the ring-down cavity 84 (360). The ring-down event lasts about ten microseconds in the present configuration, but can last a longer or shorter time in other embodiments. The light decay time is about two microseconds.

About 100 microseconds after when the ring-down event is triggered, the timing circuit 260 directs the optical modulators 60, 68 to recommence allowing the working beam 52 through to the ring-down cavity 84 (370). It is then determined if sufficient ring-down data has been collected (380). The CRDS system 20 is configured in this embodiment to collect data from 500 ring-down events. If the data from 500 ring-down events has been captured, the computer 204 stops operation of the piezo driver 248, and then determines the decay rate from the ring-down event data. If, instead, it is determined at 380 that further ring-down data is to be collected, the computer 204 continues to direct the piezo driver 248 to actuate the rear cavity mirror 88*b*. As the aggregate voltage AV attains a maximum or minimum, as shown in FIG. 6E, it commences to proceed in an opposite direction (390). That is, if the aggregate voltage AV was increasing prior to achieving the maximum voltage in its range, the aggregate voltage AV then decreases back towards the voltage corresponding with the resonance length RL. Alternatively, if the aggregate voltage AV was decreasing prior to achieving the minimum voltage in its range, the aggregate voltage AV then increases back towards the voltage corresponding with the resonance length RL. In this manner, ring-down events are triggered in both directions.

The ring-down event data (that is, the light intensities during the ring-down events) is collected as quickly as possible, as various outputs can drift. For example, the piezo actuators 252 can have a settling time referred to as piezo creep.

The ring-down event data for light intensity decay in the ring-down cavity collected in one direction can yield an error that is opposite to the error that can occur in the ring-down event data collected in the other direction. Thus, it has been found that, by averaging the data of the ring-down events can lead to more accurate results.

A decay constant defined as the length of time for the intensity to drop to 1/e (equal to approximately 0.37) of the starting intensity or some other level can be determined and then compared to a baseline decay time without the sample to determine how much light is being absorbed by the gaseous sample. The acceleration in the ring down is attributed to the presence of the gaseous sample in the ring-down cavity 84. Using the measured decay times, an absorption coefficient can be calculated for the frequency/wavelength.

The above method 300 enables the laser to be tuned and set, and the ring-down cavity 84 to be tuned to the laser and set, as opposed to constantly tracking the laser tuning and the tuning of the ring-down cavity 84. Further, by actuating at least one of the cavity mirrors relative to one another through effectively continuous motion, the need to employ an expensive piezo driver with microvolt resolution can be avoided. Still further, as the voltage generated by the piezo driver is swept over a small range, the ring-down event data can be collected over a relatively short duration of time (a couple of seconds, in the present embodiment).

Use of the centering method enables more accurate sampling of the peak near the resonance point, giving a much tighter resolution and a smaller standard deviation.

The process is repeated for lights of multiple frequencies to generate an absorption spectrum for the gaseous sample. For example, the light generated by the $CO_2$ laser 24 provides absorption coefficients for a range of frequencies. Similarly, absorption coefficients can be generated for a range of frequencies for the light from the carbon-13 $O_2$ laser 28. In this manner, an absorption spectrum can be developed for the sample.

In another alternative embodiment, the timed location of resonance peaks can be determined and then the timed location of when the threshold intensities are achieved can be registered. These timed locations can be employed as a proxy for the detection of the threshold intensity and proximity of the cavity length to the resonance length.

While, in the above-described embodiment, the light sources are two lasers that produce light in the mid-infrared range, it will be appreciated that other light sources can be employed. For example, a laser producing light in the visible spectrum or a near-infrared laser can be employed. Further, in some scenarios, the CRDS system can include only one laser, or three or more lasers, to generate the working beam.

Electro-optic modulators can be used in place of acousto-optic modulators.

The acousto-optic modulators can be configured so that the frequency of the working beam is shifted up or down. As long as the net frequency shift effected by the acousto-optic modulators shifts the frequency of the working beam significantly away from the frequency of the working beam being generated by the laser(s) so that the reflected light is outside of the bandwidth of the laser light being generated, the amount of interference between the reflected light and the generated working beam can be minimized.

In other embodiments, more than two optical modulators can be employed in a CRDS system to provide further extinguishing capacity to more quickly extinguish the working beam at the commencement of a ring-down event. Further, in further embodiments, a single optical modulator can be employed.

One or more focusing lenses can be employed in other embodiments, and translated to enable repositioning of the lenses to allow mode-matching of each wavelength of the lasers.

The same approach can be adopted for other types of resonant cavities, and particularly optical resonant cavities.

Other types of events can be triggered as the cavity length is proximal to the resonance length of the cavity for the particular selected wavelength.

Analysis of the gaseous samples can be performed at pressure levels other than one atmosphere in other embodiments. The breadth of the absorption spectrum may change accordingly.

Although specific advantages have been enumerated above, various embodiments may include some, none, or all of the enumerated advantages.

While, in the above-described embodiment, the resonant cavity is a ring-down cavity, in other embodiments, other types of resonant cavities can be employed.

Persons skilled in the art will appreciate that there are yet more alternative implementations and modifications possible, and that the above examples are only illustrations of one or more implementations. The scope, therefore, is only to be limited by the claims appended hereto.

LIST OF REFERENCE NUMERALS

20 CRDS system
24 $CO_2$ laser
28 carbon-13 $O_2$ laser
32 first laser beam
36 second laser beam
40 mirror
44 beam splitter 48 sampling beam
52 output beam
56 fast infrared detector
60 first optical modulator
64 mirror
68 second optical modulator
72 focusing lens
76 mirror
80 ring-down chamber
84 ring-down cavity
88 cavity mirror
88a front cavity mirror
88b rear cavity mirror
92 mirror mounts
96 micrometer
96a mechanized micrometer
96b piezoelectric micrometer
100 liquid nitrogen-cooled detector
104 thermal desorption tube
108 receiving end
112 pneumatic system
116 nitrogen gas source
120 conduit
120a gas intake line
120b desorption tube line
120c sample outlet line
124 solenoid valve
124a gas inlet valve
124b auxiliary gas inlet valve
124c gas intake line valve
124d cavity inlet valve
124e pathing valve
124f forward valve
124g rearward valve
124h sample outlet valve
124i cavity outlet valve
124j vacuum cutoff valve
124k vacuum intake valve
128 pressure meter
130a, 130b filter
132 heater
136 mass flow controller
140 outlet line
144 pressure meter
148 vacuum pump
150 pump intake line
200 electronic control subsystem
204 computer
205 processor
206 storage
208 RF driver
212 grating actuator
216 output coupler piezo
220 high-voltage amplifier
224 DAQ card
228 actuator driver
232 amplifier
236 oscilloscope
240 temperature controller
244 relay board
248 three-channel piezo driver
252 piezo actuator
256 RF driver
260 timing circuit
264 digitizer
CL cavity length
$P_1, P_2, P_3, P_4, P_5$ peaks
RL, $RL_1$, $RL_2$ resonance length
t time
V voltage
300 method
310 generate & transmit waveform to piezo driver
320 shift waveform until resonance length is centered
330 determine positions of threshold intensity
340 actuate mirror in first or second direction through resonance length
350 extinguish light at position of threshold intensity
360 collect ring-down data
370 recommence illuminating cavity
380 sufficient data collected?
390 change to other direction
SV sinusoidal waveform voltage
T period
BV base voltage
AV aggregate voltage
$t_1, t_2, t_3$ times

What is claimed is:

1. A method of tuning a resonant cavity, comprising:
actuating a first mirror at a first end of a resonant cavity to move in a direction between a first position relative to a second mirror at a second end of the resonant cavity, at which a cavity length between the first mirror and the second mirror is less than a resonance length for a laser beam, and a second position relative to the second mirror, at which the cavity length is greater than the resonance length;
triggering an event when the cavity length is proximal to the resonance length; and
continuing to actuate the first mirror in the direction between the first position and the second position during the event.

2. The method of claim 1, wherein the event is a first event, wherein the direction is a first direction, and wherein the method further comprises after the continuing:
actuating the first mirror to move in a second direction opposite the first direction and towards the first position;
triggering a second event when the cavity length is proximal to the resonance length; and
continuing to actuate the first mirror in the second direction between the second position and the first position during the second event.

3. The method of claim 2, further comprising:
repeatedly actuating the first mirror to move in the first direction and the second direction;
triggering events when the cavity length is proximal to the resonance length; and
continuing to actuate the first mirror during the events.

4. The method of claim 3, further comprising:
applying a voltage waveform to at least one piezo actuator coupled to the first mirror to actuate the first mirror between the first position and the second position.

5. The method of claim 4, wherein the waveform is sinusoidal.

6. The method of claim 4, further comprising:
adding a base voltage to the waveform voltage applied to the at least one piezo actuator.

7. The method of claim 6, further comprising:
controlling the base voltage to locate a light intensity peak via a light detector coupled to the resonant cavity, the peak light intensity occurring at the resonance length.

8. The method of claim 7, further comprising:
selecting an amplitude for the voltage waveform applied to the at least one piezo actuator that actuates the first mirror less than one wavelength of a laser beam illuminating the resonant cavity; and controlling the base voltage so that two light intensity peaks are detected during each period of the voltage waveform.

9. The method of claim 8, further comprising:
controlling the base voltage so that adjacent light intensity peaks are spaced by one half of a period of the voltage waveform.

10. The method of claim 8, further comprising:
triggering the events to occur when a detected light intensity achieves a threshold intensity.

11. The method of claim 10, wherein the events are ring-down events.

12. The method of claim 11, wherein the light detector is coupled to a timing circuit, the timing circuit being coupled to one of an optical modulator and a laser to extinguish the laser beam from the laser or detune the laser for the resonant cavity.

13. The method of claim 12, further comprising:
determining expected recurrence times for a threshold intensity; and
triggering the extinguishing of the laser beam or the detuning of the laser beam for the resonant cavity at the expected recurrence times for the threshold intensity.

14. The method of claim 1, further comprising:
detecting an intensity of light in the resonant cavity via a light detector,
wherein the triggering comprises triggering when a light intensity in the resonant cavity detected by the light detector achieves a threshold intensity.

15. The method of claim 14, wherein the light detector is coupled to timing circuit, the timing circuit being coupled to one of an optical modulator and a laser to extinguish the laser beam from the laser or detune the laser.

16. A method of tuning a resonant cavity, comprising:
altering a cavity length between a first mirror at a first end of a resonant cavity and a second mirror at a second end of the resonant cavity between a first cavity length that is less than a resonance length for a laser beam, and a second cavity length that is greater than the resonance length for the laser beam;
triggering an event when the cavity length is proximal to the resonance length; and
continuing to alter the cavity length towards the second cavity length during the event.

17. A method of tuning a resonant cavity, comprising:
actuating a first mirror at a first end of a resonant cavity to move in a direction between a first position relative to a second mirror at a second end of the resonant cavity, at which a cavity length between the first mirror and the second mirror is less than a resonance length for a laser beam, and a second position relative to the second mirror, at which the cavity length is greater than the resonance length;
triggering the extinguishing of a laser beam illuminating the resonant cavity or the detuning of the laser beam for the resonant cavity when the cavity length is proximal to the resonance length; and
continuing to actuate the first mirror in the direction between the first position and the second position while a light detector registers light intensity in the resonant cavity.

18. The method of claim 17, wherein the direction is a first direction, and wherein the method further comprises after the continuing:
triggering the illumination of the laser beam or the retuning of the laser beam for the resonant cavity;
actuating the first mirror to move in a second direction opposite the first direction and towards the first position;
triggering the extinguishing of the laser beam or the detuning of the laser beam for the resonant cavity; and
continuing to actuate the first mirror in the second direction between the second position and the first position while the light detector registers light intensity in the resonant cavity.

19. The method of claim 18, further comprising:
applying a sinusoidal waveform to at least one piezo actuator coupled to the first mirror to actuate the first mirror between the first position and the second position.

20. The method of claim 19, further comprising:
adding a base voltage to the waveform voltage applied to the at least one piezo actuator.

21. The method of claim 20, further comprising:
controlling the base voltage to locate a light intensity peak via a light detector coupled to the resonant cavity, the peak light intensity occurring at the resonance length.

22. The method of claim 21, further comprising:
selecting an amplitude for the voltage waveform applied to the at least one piezo actuator that actuates the first mirror less than one wavelength of a laser beam illuminating the resonant cavity; and
controlling the base voltage so that two light intensity peaks are detected during each period of the voltage waveform.

23. The method of claim 22, further comprising:
controlling the base voltage so that adjacent light intensity peaks are spaced by one half of a period of the voltage waveform.

24. The method of claim 18, wherein the cavity length being proximal to the resonance length is detected by a detected light intensity achieving a threshold intensity.

25. The method of claim 24, wherein the light detector is coupled to a timing circuit, the timing circuit being coupled to one of an optical modulator and a laser to extinguish the laser beam from the laser or detune the laser for the resonant cavity.

26. The method of claim 18, further comprising:
determining expected recurrence times for achievement of a threshold intensity as a proxy for when the cavity length is proximal to the resonance length.

\* \* \* \* \*